United States Patent
Isotani

(10) Patent No.: US 7,217,837 B2
(45) Date of Patent: May 15, 2007

(54) METHOD FOR PRODUCING ORGANIC ACID

(75) Inventor: Atsushi Isotani, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 70 days.

(21) Appl. No.: 10/976,822

(22) Filed: Nov. 1, 2004

(65) Prior Publication Data

US 2005/0070738 A1 Mar. 31, 2005

Related U.S. Application Data

(63) Continuation of application No. PCT/JP03/05826, filed on May 9, 2003.

(30) Foreign Application Priority Data

| May 10, 2002 | (JP) | .............................. 2002-135656 |
| Aug. 8, 2002 | (JP) | .............................. 2002-231740 |
| Aug. 8, 2002 | (JP) | .............................. 2002-231741 |
| Oct. 21, 2002 | (JP) | .............................. 2002-305989 |

(51) Int. Cl.
*C07C 51/42* (2006.01)

(52) U.S. Cl. .................................................... 562/593

(58) Field of Classification Search ...................... None
See application file for complete search history.

(56) References Cited

U.S. PATENT DOCUMENTS

| 3,818,081 A | 6/1974 | Adamek |
| 3,833,646 A | 9/1974 | Norton |
| 5,210,292 A | 5/1993 | Park et al. |
| 5,958,744 A | 9/1999 | Berglund et al. |

FOREIGN PATENT DOCUMENTS

| EP | 0 590 856 A1 | 4/1994 |
| EP | 0 608 975 A1 | 8/1994 |
| JP | 61-50937 A | 3/1986 |
| JP | 63-264546 | 11/1988 |

*Primary Examiner*—Paul A. Zucker
(74) *Attorney, Agent, or Firm*—Oblon, Spivak, McClelland, Maier & Neustadt, P.C.

(57) ABSTRACT

A free organic acid can be produced efficiently at a low cost, by subjecting an ammonium salt of organic acid A such as a dicarboxylic acid, a tricarboxylic acid or an amino acid, to reactive crystallization with an acid B, such as a monocarboxylic acid, wherein organic acid A and acid B satisfy the following formula (1):

$$pKa(A) \leq pKa(B) \qquad (1)$$

where $pKa(A)$ and $pKa(B)$ represent ionization indices of organic acid A and acid B, respectively, provided that when they have plural values, they represent the minimum pKa among them, to separate free organic acid A in solid form.

40 Claims, 6 Drawing Sheets

METHOD FOR PRODUCING ORGANIC ACID

CROSS REFERENCES TO RELATED APPLICATIONS

This application is a continuation of International Patent Application No. PCT/JP03/05826, filed on May 9, 2003, and claims priority to Japanese Patent Application No. 2002-135656, filed on May 10, 2002, Japanese Patent Application No. 2002-231740, filed on Aug. 8, 2002, Japanese Patent Application No. 2002-231741, filed on Aug. 8, 2002, and Japanese Patent Application No. 2002-305989, filed on Oct. 21, 2002.

TECHNICAL FIELD

The present invention relates to method for producing an organic acid having a high melting point such as a dicarboxylic acid, a tricarboxylic acid or an amino acid (hereinafter sometimes generally referred to as organic acid A). More particularly, it relates to a method for producing an organic acid comprising a novel separation/purification step of an organic acid, which is useful in a case where a biogenic material such as glucose, fructose or cellulose, is produced by bioconversion.

BACKGROUND ART

A carboxylic acid such as succinic acid or its derivative is widely used as a material for a polymer such as a polyester or a polyamide, particularly as a material for a biodegradable polyester, or as a material for food products, pharmaceuticals and cosmetics. Further, a tricarboxylic acid such as citric acid is widely used as a food additive, etc. In recent years, particularly succinic acid is expected to be a material for a biodegradable polymer, together with lactic acid.

Succinic acid has heretofore been industrially obtained by hydrogenation of maleic acid, and the maleic acid is a material derived from petroleum. Accordingly, as a technique to produce an organic acid such as succinic acid, malic acid, tartaric acid or citric acid from a material derived from a plant, a technique to utilize a fermentation operation has been studied. Further, an amino acid has already been produced by a fermentation method, but separation and purification of an amino acid have been carried out usually by isoelectric point precipitation employing sulfuric acid.

Further, such an organic acid as a dicarboxylic acid or a tricarboxylic acid has at least two carboxyl groups, or carboxyl groups and an amino group, as functional groups. Due to such hydrogen bonds, its melting point is usually high (usually at least 120° C.), and in its production process, a distillation operation as a common separation/purification method, can not be employed. Further, in the production of such an organic acid by fermentation, neutralization is usually required, since a microorganism such as fungus or mold to be used for the fermentation does not show an adequate activity usually under a low pH condition. Accordingly, an organic acid obtainable from a fermenter, is usually in the form of a salt with an alkali used for the neutralization. This is a factor which makes the separation/purification of such an organic acid more difficult.

Heretofore, a method employing electrodialysis (JP-A-2-283289) is available as a common separation/purification method for a salt of an organic acid formed by fermentation. However, the electrodialysis has a problem that since the apparatus is large in proportion to production scale, and the scale merit is small even by production on an industrial scale, and consequently the cost tends to be high.

Further, a method of employing an ion exchange resin has been proposed (U.S. Pat. No. 6,284,904). However, in this method, a salt of a strong acid and strong base (such as NaCl) will be formed at the time of regenerating the ion exchange resin, and eventually, this salt is required to be disposed or to be treated by electrodialysis.

Further, a method of decomposing calcium succinate with sulfuric acid has been proposed (JP-A-3-030685). However, in this method, calcium sulfate will be formed in a large amount as a byproduct, and its treatment is problematic.

Further, as an effective method, a method of carrying out reactive crystallization by an exchange reaction of a salt by means of sulfuric acid has been proposed (JP-A-2001-514900, U.S. Pat. No. 5,958,744). Namely, this is a method for precipitating and separating an organic acid by carrying out reactive crystallization by adding sulfuric acid to an ammonium salt of an organic acid.

In this method, a soluble amount of the ammonium salt of the organic acid will remain in the crystallization mother liquor after separating the organic acid by crystallization, and ammonium sulfate will also be contained in this crystallization mother liquor. In order to increase the recovery rate of the entire process, it is necessary to recover such an ammonium salt of the organic acid remaining in the crystallization mother liquor, but even if a crystallization operation is further applied to this crystallization mother liquor, it is extremely difficult to separate ammonium sulfate in solid form, while permitting the ammonium salt of the organic acid to remain in the liquid. Otherwise, even if it is attempted to carry out separation by a gas/liquid separation operation such as distillation, the ammonium salt of the organic acid and ammonium sulfate have very high melting points, and under such a high temperature condition as to vaporize these compounds, the ammonium salt of the organic acid will undergo a dehydration reaction, and it would be impossible to recover the organic acid. Further, by this method, a special installation has been required to carry out pyrolysis of ammonium sulfate at a temperature of at least 300° C. in order to recover and reuse sulfuric acid from ammonium sulfate.

It is an object of the present invention to solve such conventional problems and to provide a novel method for producing organic acid A having a high purity by separating and purifying free organic acid A from a salt of organic acid A formed by a fermentation method by bioconversion of a carbon source in the presence of a neutralizing agent.

Another object of the present invention is to provide a method for producing organic acid A efficiently at a low cost with a low level of waste in consideration of environment, by decomposing and reusing a byproduct salt formed in the above-mentioned novel method for producing organic acid A.

DISCLOSURE OF THE INVENTION

As a result of an extensive research on the above problems, the present inventor has paid particular attention to characteristics of organic acid A to be obtained in the present invention such that its solubility in a monocarboxylic acid (hereinafter sometimes referred to as acid B) being a weak acid such as acetic acid or propionic acid, is generally low and its temperature dependency is high, and an ammonium salt of organic acid A has a high solubility in acid B. It has been found that by utilizing such characteristics, it is possible to separate the ammonium salt of organic acid A which should be hardly decomposable when judged solely from pKa (Ka: dissociation constant, pKa=$\log_{10}$Ka), in the form of an acid, by reactive crystallization by means of acid B, and it is possible to decompose an ammonium salt of acid B formed as a byproduct, under a relatively mild heating condition, and it is possible to reuse ammonia obtained by the decomposition.

In the present invention, "an ammonium salt" means a mono-, di- and/or tri-ammonium salt, unless otherwise defined.

It is a well known fact that in general, a salt of a weak acid can be decomposed by a strong acid by means of an exchange reaction of the salt to produce a salt of the strong acid as a byproduct and to obtain the weak acid. This is the above-mentioned conventional method for carrying out an exchange reaction of a salt by means of sulfuric acid (U.S. Pat. No. 5,958,744). Further, also in the method of employing an ion exchange resin, the ion exchange resin is required to be an acid stronger than a dicarboxylic acid or a tricarboxylic acid. However, as mentioned above, in such a method, a salt of an acid stronger than the desired organic acid will be formed as a byproduct.

When comparison is made with respect to pKa as an index for the acid intensity in an acid/base exchange reaction, for example, pKa of succinic acid and acetic acid is as shown below, and it is evident that diammonium succinate (secondary kPa) is capable of an acid/base exchange reaction with acetic acid, but monoammonium succinate is hardly capable of such an acid/base exchange reaction with acetic acid.

| | |
|---|---|
| Succinic acid primary pKa: | 4.21 |
| Succinic acid secondary pKa: | 5.64 |
| Acetic acid pKa: | 4.76 |

Accordingly, as mentioned above, it has been common to employ a method of using a strong acid or an ion exchange resin having a strong acidity. As shown in JP-A-2001-514900, in the crystallization employing an inorganic acid, it is usually required to have a high recovery rate by a single stage of crystallization, since an ammonium salt of the inorganic acid is usually non-volatile. Accordingly, in the case of succinic acid, primary pKa is 4.21, whereby the pH must be smaller than 2.1 in order to obtain a sufficient recovery rate. Thus, in JP-A-2001-514900, sulfuric acid is used for the reactive crystallization. In this method, the pH is required to be from 1.5 to 1.8.

Whereas, the present inventor has discovered that organic acid A which is difficult to obtain solely by an acid/base reaction, can be easily separated and purified by reactive crystallization by means of acid B such as a monocarboxylic acid, which is an acid weaker than the desired organic acid A.

Namely, paying an attention to the fact that organic acid A obtainable as a result of bioconversion in the presence of a neutralizing agent, has a high solubility as an ammonium salt of organic acid A and a low solubility as ammonia free organic acid A, in acid B as a weak acid, the present inventor has found a fact that there is a region wherein it is soluble as an ammonium salt of organic acid A, but insoluble as ammonia free organic acid A, in acid B.

On the other hand, acid B functions as a proton source, whereby by permitting a sufficient amount of acid B to be coexistent, to lower the pH, it is possible to convert the ammonium salt of organic acid A to ammonia free organic acid A by an acid/base reaction with acid B. If such ammonia free organic acid A is present beyond the solubility, the ammonia free organic acid A precipitates. At that time organic acid A in the form of ammonium salt has a sufficiently high solubility in acid B and will not precipitate at the same time.

On the basis of such discoveries, the present inventor has succeeded in separating organic acid A which used to be difficult to obtain solely by an acid/base reaction, in solid form, by reactive crystallization by means of acid B which is a weaker acid than organic acid A.

On the other hand, in such a case, there may be a case where the recovery per stage tends to be poor as compared with conventional crystallization employing a strong acid. Therefore, it is preferred that the ammonium salt of acid B formed as a byproduct and the ammonium salt of organic acid A, contained in the mother liquor, are separated and recovered from the mother liquor and recycled, for industrial operation. Further, if the salt of acid B formed as a byproduct, is disposed, a problem of a disposed waste will be created like the conventional technique, and accordingly, it is preferred to decompose and reuse the ammonium salt of acid B formed as a byproduct.

The present inventor has found that ammonia constituting the ammonium salt of organic acid A is a volatile base, and in a case where a volatile acid, preferably a saturated monocarboxylic acid having a low boiling point such as acetic acid or propionic acid is used as acid B, it is possible to vaporize the ammonium salt of acid B. By this operation, they have succeeded in recovering organic acid A from the mother liquor obtained by reactive crystallization.

Thus, the present invention is characterized by having the following features.

1. A method for producing organic acid A, which comprises subjecting an ammonium salt of organic acid A to reactive crystallization by means of acid B satisfying the following formula (1), to separate organic acid A in solid form:

$$pKa(A) \leq pKa(B) \qquad (1)$$

where pKa(A) and pKa(B) represent ionization indices of organic acid A and acid B, respectively, provided that when they have plural values, they represent the minimum pKa among them.

2. The method according to Item 1, wherein acid B is volatile.

3. The method according to Item 1 or 2, wherein organic acid A is an organic acid having a melting point of at least 120° C.

4. The method according to Item 1 or 2, wherein organic acid A is a $C_{4-12}$ dicarboxylic or tricarboxylic acid, or a $C_{4-12}$ amino acid.

5. The method according to any one of Items 1 to 4, wherein acid B is a monocarboxylic acid.

6. The method according to any one of Items 1 to 4, wherein acid B is acetic acid or propionic acid.

7. The method according to any one of Items 1 to 6, wherein the reactive crystallization is carried out in a single stage or multi-stages, and the pH is from 2.1 to 6.5 at least in one stage.

8. The method according to any one of Items 1 to 7, wherein the ammonium salt of organic acid A is one obtained via a bioconversion step in which a carbon source is converted by a microorganism in the presence of at least one neutralizing agent selected from the group consisting of ammonia, ammonium carbonate and urea.

9. The method according to any one of Items 1 to 7, wherein the ammonium salt of organic acid A is one obtained in the form of an aqueous solution of the ammonium salt of organic acid A in such a manner that a reaction solution containing an alkali metal and/or alkaline earth metal salt of organic acid A is obtained via a bioconversion step in which a carbon source is converted by a microorganism in the presence of at least one neutralizing agent selected from the group consisting of an alkali metal hydroxide, an alkaline earth metal hydroxide, an alkali metal carbonate and an alkaline earth metal carbonate; ammonia and carbon dioxide, and/or ammonium carbonate, is added to said reaction solution containing an alkali metal and/or alkaline earth metal salt of organic acid A to carry out reactive crystallization to precipitate an alkali metal and/or alkaline earth metal carbonate (Solvay process step); and the precipitated carbonate is separated.

10. The method according to Item 8 or 9, which includes a concentration step of concentrating the reaction solution obtained in the bioconversion step, and wherein a concentrate obtained in the concentration step is subjected to the reactive crystallization.

11. The method according to any one of Items 1 to 7, wherein the ammonium salt of organic acid A is one formed in a chemical process.

12. The method according to any one of Items 1 to 11, wherein organic acid A precipitated by the reactive crystallization is separated; after the separation, an ammonium salt of acid B in the crystallization mother liquor is decomposed by a decomposition step to obtain acid B; and the obtained acid B is recycled for use as a solvent for the reactive crystallization.

13. The method according to Item 12, wherein organic acid A precipitated by the reactive crystallization is separated; after the separation, the crystallization mother liquor is concentrated by vaporizing acid B therefrom; and then, the acid B and its ammonium salt are decomposed/vaporized in order to recover organic acid A and its ammonium salt.

14. The method according to Item 13, wherein the vaporization of acid B is carried out at a temperature of not higher than the melting point of the ammonium salt of acid B.

15. The method according to Item 13 or 14, wherein the decomposition/vaporization of the acid B and its ammonium salt are carried out by heating under a reduced pressure of from 0.001 mmHg to 200 mmHg.

16. The method according to any one of Items 12 to 15, wherein the decomposition step comprises a heating step of heating a liquid comprising the ammonium salt of acid B, an alkali metal and/or alkaline earth metal salt of acid B, and water, and withdrawing a gas of a basic aqueous solution, and a step of subjecting the basic aqueous solution withdrawn from the heating step, directly or after condensation, to gas/liquid separation, gas/solid separation or gas/liquid/solid separation at a temperature of not higher than the melting point of the ammonium salt of acid B.

17. The method according to any one of Items 12 to 15, wherein the decomposition step comprises a heating step of supplying a liquid comprising the ammonium salt of acid B, an alkali metal and/or alkaline earth metal salt of acid B, and water, to a distillation column having at least two plates as the real number of plates, and withdrawing a gas of a basic aqueous solution from the top of the distillation column.

18. The method according to Item 17, wherein in the heating step, the liquid comprising the ammonium salt of acid B, an alkali metal and/or alkaline earth metal salt of acid B, and water, is supplied to a site of the distillation column having at least two plates as the real number of plates, where the temperature is not higher than the melting point of the ammonium salt of acid B.

19. The method according to any one of Items 16 to 18, wherein the alkali metal and/or alkaline earth metal constituting the alkali metal and/or alkaline earth metal salt of acid B, is at least one member selected from the group consisting of Na, K, Ca and Mg.

20. The method according to any one of Items 16 to 19, wherein the liquid after withdrawing the gas of a basic aqueous solution in the heating step, is subjected to a separation step which is carried out under reduced pressure or atmospheric pressure at a temperature of at least 125° C., to separate and recover acid B.

21. The method according to Item 20, wherein the residual liquid after the separation step is mixed with a system containing water to hydrolyze an amide compound formed as a byproduct in the heating step and the separation step and then recycled to the heating step.

22. The method according to any one of Items 1 to 10 and 12 to 21, wherein the ammonium salt of organic acid A is one obtained as a reaction solution containing the ammonium salt of organic acid A via a bioconversion step in which conversion is carried out by a microorganism by means of ammonia as a neutralizing agent; organic acid A precipitated by the reactive crystallization carried out by adding acid B, is separated; after the separation, the ammonium salt of acid B in the crystallization mother liquor, is decomposed to obtain ammonia; and the ammonia is used as a neutralizing agent for the bioconversion step.

23. The method according to any one of Items 1 to 10 and 12 to 22, wherein the ammonium salt of organic acid A is one obtained in the form of an aqueous solution of the ammonium salt of organic acid A in such a manner that a reaction solution containing an alkali metal and/or alkaline earth metal salt of organic acid A is obtained via a bioconversion step in which a carbon source is converted by a microorganism in the presence of at least one neutralizing agent selected from the group consisting of an alkali metal hydroxide, an alkaline earth metal hydroxide, an alkali metal carbonate and an alkaline earth metal carbonate; ammonia and carbon dioxide, and/or ammonium carbonate, is added to said reaction solution containing an alkali metal and/or alkaline earth metal salt of organic acid A to carry out reactive crystallization to precipitate an alkali metal and/or alkaline earth metal carbonate (Solvay process step); and the precipitated carbonate is separated; organic acid A precipitated by the reactive crystallization carried out by adding acid B, is separated; after the separation, the ammonium salt of acid B in the crystallization mother liquor, is decomposed to obtain ammonia; and the ammonia is used as an ammonia source for the Solvay process step.

24. The method according to any one of Items 1 to 23, wherein the reactive crystallization is carried out in multistages, and in reactive crystallization in the second or subsequent stage, the crystallization mother liquor after separating the precipitated organic acid A is, directly or after concentrating the ammonium salt of acid B by vaporization of the reactive crystallization solvent containing acid B, or after separating organic acid A or its salt dissolved in the mother liquor, recycled to a crystallizer for reactive crystallization in a preceding stage.

25. In a process for separating and recovering acid B and ammonia by decomposing an ammonium salt of acid B to acid B and ammonia, a method for decomposing the ammonium salt of acid B, which comprises a heating step of heating a liquid comprising the ammonium salt of acid B, an alkali metal and/or alkaline earth metal salt of acid B, and water, and withdrawing a gas of a basic aqueous solution, and a step of subjecting the basic aqueous solution withdrawn from the heating step, directly or after condensation, to gas/liquid separation, gas/solid separation or gas/liquid/solid separation at a temperature of not higher than the melting point of the ammonium salt of acid B.

26. In a process for separating and recovering acid B and ammonia by decomposing an ammonium salt of acid B to acid B and ammonia, a method-for decomposing the ammonium salt of acid B, which comprises a heating step of supplying a liquid comprising the ammonium salt of acid B, an alkali metal and/or alkaline earth metal salt of acid B, and water, to a site of a distillation column having at least two plates as the real number of plates, where the temperature is not higher than the melting point of the ammonium salt of acid B, and withdrawing a gas of a basic aqueous solution from the top of the distillation column.

27. The method according to Item 25 or 26, wherein the alkali metal and/or alkaline earth metal constituting the alkali metal and/or alkaline earth metal salt of acid B, is at least one member selected from the group consisting of Na, K, Ca and Mg.

28. The method according to any one of Items 25 to 27, wherein acid B is at least one member selected from the group consisting of formic acid, acetic acid, propionic acid and butyric acid.

29. The method according to any one of Items 25 to 28, which comprises a step of recovering acid B, wherein the liquid after withdrawing the gas of a basic aqueous solution in the heating step, is subjected to a separation step which is carried out under reduced pressure or atmospheric pressure at a temperature of at least 125° C., to separate and recover acid B.

30. The method according to any one of Items 25 to 29, wherein the residual liquid after the separation step is mixed with a system containing water to hydrolyze an amide compound formed as a byproduct in the heating step and the separation step and then recycled to the heating step.

31. Organic acid A produced by a method as defined in any one of Items 1 to 24.

32. A polymer prepared by using, as a material, organic acid A produced by a method as defined in any one of Items 1 to 24.

Figure 1:
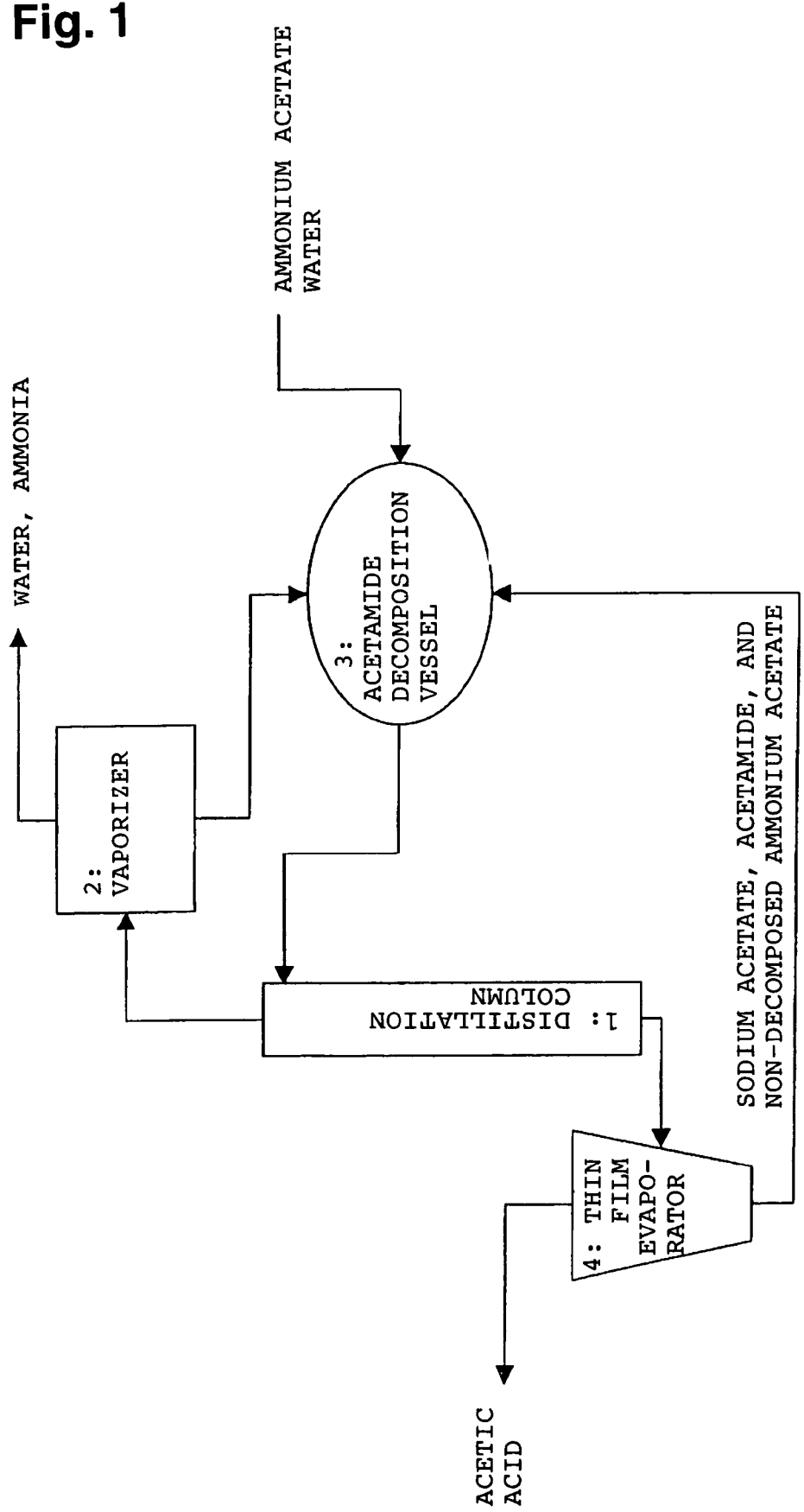
FIG. 1 is a schematic flowchart showing the construction of an apparatus suitable for carrying out the method for decomposition of an ammonium salt of acid B of the present invention.

MEANING OF SYMBOLS 1, 1A, 1B: Distillation columns 2: Vaporizer
3: Acetamide decomposition vessel
4: Thin film evaporator 5: Flash drum
10: Distillation column 12: Oil bath
13: Flask 16: Feed material vessel 17: Preheater

EMBODIMENTS OF THE INVENTION

Now, embodiments of the method for producing an organic acid according to the present invention, will be described in detail.

Formation of an Ammonium Salt of Organic Acid A

Organic acid A to be produced by the present invention may, for example, be one having a melting point which is preferably at least 120° C. Its carbon number is preferably from 4 to 12, and it is preferably one having a straight chain form. A dicarboxylic acid or a tricarboxylic acid may, for example, be mentioned as a typical example. Preferred is one having two or three carboxyl groups bonded to a saturated or unsaturated aliphatic hydrocarbon, and it may have a branched chain or cyclic structure, and it may have a substituent. Further, organic acid A includes an amino acid having a melting point which is preferably at least 120° C.

Specifically, organic acid A may, for example, be succinic acid, fumaric acid, maleic acid, malic acid, tartaric acid, asparaginic acid, glutaric acid, glutamic acid, adipic acid, suberic acid, citric acid, itaconic acid, terephthalic acid, phenylalanine, tryptophan, asparagine, glutamine, valine, isoleucine, leucine, histidine, methionine or tyrosine. These acids may be a mixture of two or more of them. Among them, preferred as organic acid A is, for example, succinic acid, adipic acid, glutamic acid, suberic acid, tartaric acid or citric acid. Particularly preferred is succinic acid, adipic acid, glutamic acid or suberic acid. Such organic acid A may be formed, for example, by bioconversion using a carbon source as the starting material. As the carbon source, a fermentable carbohydrate, such as a carbohydrate such as galactose, lactose, glucose, fructose, glycerol, sucrose, saccharose, starch or cellulose, or a polyalcohol such as glycerine, mannitol, xylitol or ribitol, may, for example, be used. Among them, glucose, fructose or glycerol is preferred. Particularly preferred is glucose. As a broader plant-derived material, cellulose as the main component for paper, is preferred. Further, a starch-succharized liquid or treacle containing the above-mentioned fermentable carbohydrate, may also be used. Such fermentable carbohydrates may be used alone or in combination as a mixture of two or more of them.

The microorganism to be used for such bioconversion is not particularly limited so long as it has an ability to produce organic acid A. For example, anaerobic bacteria such as genus *Anaerobiospirillum* (U.S. Pat. No. 5,143,833), facultative anaerobic bacteria such as genus *Actinobacillus* (U.S. Pat. No. 5,504,004) or genus *Escherichia* (U.S. Pat. No. 5,770,435), or aerobic bacteria such as genus *Corynebacterium* (JP 11113588) may, for example, be used. The reaction conditions such as the reaction temperature, pressure, etc., in the bioconversion, depend upon the activities of the fungus, mold, etc. to be selected, but suitable conditions to obtain the corresponding organic acid A may be suitably selected depending upon the respective cases.

In the above bioconversion, if the pH becomes low, the metabolic activities of the microorganism tend to be low, or the microorganism tends to stop its activities, whereby the production yield is likely to deteriorate, or the microorganism is likely to die. Therefore, a neutralizing agent is used. Usually, the pH in the reaction system is measured by a pH sensor, and the pH is adjusted to be within a prescribed pH range, every time when a neutralizing agent is added. In the present invention, the method for adding a neutralizing agent is not particularly limited, and it may be continuous addition or intermittent addition.

The neutralizing agent may, for example, be ammonia, ammonium carbonate, urea, an alkali metal hydroxide, an alkaline earth metal hydroxide, an alkali metal carbonate or an alkaline earth metal carbonate. Preferred is ammonia, ammonium carbonate or urea. Namely, as mentioned above, in a case where an alkali metal or alkaline earth metal hydroxide or an alkali metal or an alkaline earth metal carbonate is employed, an alkali metal or alkaline earth metal salt of acid B will be formed as a byproduct in the reactive crystallization by means of acid B, and the alkali metal or alkaline earth metal used for neutralization can not directly be recovered. Accordingly, in the Solvay process step, a step of obtaining an ammonia salt of organic acid A will be required. Further, the alkali metal or alkaline earth metal hydroxide may, for example, be NaOH, KOH, $Ca(OH)_2$, $Mg(OH)_2$, or a mixture thereof. The alkali metal or alkaline earth metal carbonate may, for example, be $Na_2CO_3$, $K_2CO_3$, $CaCO_3$, $MgCO_3$, $NaKCO_3$ or a mixture thereof.

The pH value to be adjusted by such a neutralizing agent, is adjusted depending upon the type of the fungus or mold to be used, within a range where its activities are most effectively obtained. Usually, the pH is within a range of from 4 to 10, preferably from 6 to 9.

The ammonium salt of organic acid A to be the starting material for organic acid A to be produced by the present invention, is not necessarily limited to one obtained by the above-mentioned bioconversion, but may be one produced or produced as a byproduct from a petrochemical process or from other various processes.

Reactive Crystallization

In general, crystallization refers to an operation to precipitate the necessary component in a state where unnecessary components are dissolved in a solvent. Whereas, in the present invention, "reactive crystallization" means an operation whereby a necessary component is obtained by a reaction and at the same time crystallization is carried out. Namely, it is meant for an operation in which crystallization of the desired product is carried out while carrying out a reaction to obtain the desired product to be crystallized. In the present invention, separation and purification of such organic acid A is carried out by reactive crystallization employing acid B which is a weaker acid than organic acid A, as mentioned above. Acid B to be used, is required to satisfy the following formula (1):

$$pKa(A) \leq pKa(B) \tag{1}$$

Here, in the formula (1), Ka(A) and Ka(B) represent the dissociation constants of organic acid A and acid B, respectively, and in a case where they have plural values, they represent the minimum pKa among them. Although it may depend substantially on the functional groups of organic acid A, pKa(B) is preferably larger by from 0 to 3 than pKa(A) while satisfying the above formula (1).

As an example of acid B, a preferably $C_{1-6}$, particularly preferably $C_{1-4}$, monocarboxylic acid, is preferred. Specifically, at least one member selected from formic acid, acetic acid, propionic acid, n-butyric acid and isobutyric acid, may be mentioned. Among them, acetic acid or propionic acid is preferred from the viewpoint of the low corrosiveness to the material of the apparatus and the evaporation latent heat. More preferably, it is an acid produced as a byproduct by the fungus to be used for bioconversion. For example, in the case of the fungus disclosed in JP-A-11-206385 or JP2002-34826, acetic acid is preferred. Further, acid B must be volatile, so that it can be separated from the alkali metal salt. Further, it is preferably stable against heat. Not preferred is one which has a carbon-carbon double bond or triple bond and which undergoes polymerization or decomposition under a condition of not higher than 200° C. in the presence of an alkali metal or alkaline earth metal, or one which has a peroxide as a functional group and which undergoes self decomposition under a condition of not higher than 200° C. in the presence of an alkali metal or alkaline earth metal, or one which has plural functional groups in one molecule such as lactic acid, tartaric acid or an amino acid and which forms a polymer (such as a polyester or polyamide).

As mentioned above, organic acid A is obtained from a fermenter as a dilute aqueous solution in the form of a salt with the neutralizing agent employed in the bioconversion. Accordingly, organic acid A is separated and purified from the reaction solution discharged from this fermenter, whereby organic acid A as a commercial product can be produced. Here, a case will be described in which at least one member selected from the group consisting of ammonia, ammonium carbonate and urea is used as a neutralizing agent (hereinafter sometimes referred to as an ammonia type neutralizing agent).

In such a case, the reaction solution from the fermenter containing an ammonium salt of organic acid A is usually a dilute aqueous solution, and this reaction solution is preferably concentrated. The method for concentration is not particularly limited, and, for example, evaporation, crystallization by means of an alcohol or the like, membrane separation utilizing reverse osmosis, or electrodialysis by means of an ion exchange membrane, may be mentioned. Among them, electrodialysis has a difficulty such that a scale merit can not be obtained, and the cost for the apparatus or operation is high, as mentioned above. In the crystallization by means of an alcohol or the like, an extradistillation apparatus to recover the alcohol will be required. From such a viewpoint and from the viewpoint of the cost, distillation is preferred, and preferably, distillation by means of a multi-effect evaporator may be mentioned.

With respect to the degree for concentration of the reaction solution, even in the case of an aqueous solution having a high concentration, for example, a highly concentrated aqueous solution in which the concentration of an ammonium salt of organic acid A is at least 40 wt %, concentration may be carried out until the ammonium salt of organic acid A precipitates in solid form. In the case of a highly concentrated aqueous solution, there is a merit such that dissolution into acid B is easy, and the operation is easy as compared with a slurry or solid. On the other hand, in a case where the ammonium salt of organic acid A is made into solid form, mixing of water and acid B can be avoided, and there is a merit such that even if excess ammonia or an ammonium salt of acid B formed as byproduct, is present, such ammonia or an ammonium salt can be removed by vaporization in the drying/evaporation step, for example, by means of a thin film evaporator. The degree for concentration is suitably determined so that the entire process including the reaction conditions for bioconversion which are influential over the types and amounts of impurities, can be optimized.

Depending upon the type of organic acid A or the type of acid B, the reactive crystallization may be carried out in a single stage or in multiple stages (a plurality of stages). It is usually carried out in multi-stages from restrictions such as initial investment, operational conditions or recovery rate, and it is particularly preferably carried out in from 2 to 4 stages in many cases. Further, in a case where multi-stage crystallization is carried out, one having a pH of not higher than 7, corresponds to the reactive crystallization in the present invention. When the pH is not higher than 7, for example, if organic acid A is succinic acid, a monoammonium salt of succinic acid can be obtained from a diammonium salt of succinic acid, whereby in the subsequent reactive crystallization, succinic acid can be obtained at a higher recovery rate. Thus, this corresponds to the reactive crystallization.

In the final stage of the reactive crystallization (in the single stage when the reactive crystallization is carried out in a single stage), the amount of acid B to be added to the reaction solution may be an amount such that organic acid A will precipitate by the addition of acid B, i.e. an amount which is sufficient for formation of organic acid A by an acid/base reaction of acid B with an ammonium salt of organic acid A and which is sufficient to precipitate formed organic acid A without dissolution. The amount of acid B varies depending upon the type and pKa of acid B, the type and pKa of organic acid A, the degree of concentration of the fermentation reaction solution, etc., and is not particularly limited. From the viewpoint of the operation efficiency, precipitation efficiency, etc., the amount of acid B to be added is from about 1 to 100 times by mol, preferably from 1.5 to 30 times by mol, more preferably from 2 to 20 times by mol, to the ammonium salt of organic acid A, when the concentrate is in solid form.

Further, the system in which the above organic acid A precipitates, may contain water. Especially under a condition where ammonia is present in a large amount, in order to dissolve an ammonium salt of acid B to be formed as a byproduct, it may be desirable for the system to contain water in many cases, and water may be added also when the amount of acid B to be used is small.

There is no particular limitation to the conditions for the reactive crystallization of organic acid A by the addition of acid B. However, usually, acid B may be added to the concentrate of the above-mentioned reaction solution, followed by heating and then the mixture is left to cool. Otherwise, water may be added to dissolve the ammonium salt of organic acid A, and then acid B is added for crystallization. The latter method is effective for organic acid A which has a low solubility in water in the form of an acid and will have a high solubility when formed into a salt, so that the difference in solubility is remarkable, like glutamic acid.

The heating temperature, the heating time and the cooling temperature at the time of crystallization may vary depending also on the type of organic acid A in the concentrate, the type and the amount to be added of acid B, etc. However, it is usually preferred that it is completely dissolved at a temperature of from 60 to 130° C., and then left to cool at a temperature of at most 50° C., preferably at most 40° C. and at least 0° C., preferably at least 10° C.

In a case where acetic acid is employed as acid B, its melting point is 16° C., but the cooling temperature may be lowered to close to 10° C. by an influence of lowering of the solidification point. For a practical process, the cooling temperature is preferably at least 15° C. as a safe condition to avoid solidification of acid B. Especially in the case of a continuous process, it is preferred that the temperature of utility (cooling medium) of a heat exchanger has a temperature difference by about 10° C. from the objective temperature, whereby the cooling temperature is more preferably at least 20° C. when acid B is acetic acid.

The reactive crystallization in the present invention can be carried out in accordance with a usual method by means of a commonly employed crystallizing apparatus. However, with some organic acid A, particularly with succinic acid, the crystallization speed is slow, and accordingly, it is preferred to employ some measure to improve the amount of crystallization, such as circulating seed crystals or taking a long retention time.

By carrying out the reactive crystallization, organic acid A having a low solubility in acid B will form and precipitate by an acid/base reaction of acid B and an ammonium salt of organic acid A obtained by the bioconversion employing an ammonia type neutralizing agent. Accordingly, by separating the precipitate from this crystallization solution by e.g. filtration, organic acid A having a high purity can be recovered as the desired product. The obtained organic acid A may be purified, for example, by recrystallization employing e.g. acid B, as the case requires, to obtain a final product.

Further, in the production of organic acid A by bioconversion, depending upon the microorganism, the productivity may be changed by the neutralizing agent. Therefore, there may be a case where it is preferred to use an alkali metal and/or alkaline earth metal hydroxide or carbonate (hereinafter sometimes referred to as an alkali metal or alkaline earth metal type neutralizing agent) rather than the above ammonia type neutralizing agent, as the neutralizing agent. In a case where an alkali metal or alkaline earth metal type neutralizing agent is employed, organic acid A by bioconversion will be formed in the form of an alkali metal or alkaline earth metal salt, but the alkali metal or alkaline earth metal is not volatile, whereby it is difficult to separate organic acid A and the alkali metal or alkaline earth metal salt of acid B from the mother liquor comprising organic acid A and the alkali metal or alkaline earth metal salt of acid B formed as a byproduct by this reactive crystallization.

Therefore, in a case where an alkali metal or alkaline earth metal type neutralizing agent is employed, a Solvay method is employed as the first reactive crystallization step, wherein exchange of the bases is carried out to obtain an ammonium salt of organic acid A, and this ammonium salt of organic acid A is subjected to reactive crystallization by means of acid B in the second reactive crystallization step to obtain organic acid A. Also in this case, it is preferred to supply the reaction solution obtained in the bioconversion step to the first reaction crystallization step after concentrating it.

In the first reactive crystallization step, firstly, ammonia and carbon dioxide and/or ammonium carbonate is added to the concentrate obtained in the concentration step, to precipitate an alkali metal or alkaline earth metal carbonate from an aqueous solution of an alkali metal or alkaline earth metal salt of organic acid A. In this first reactive crystallization step, the amount of ammonia and carbon dioxide and/or ammonium carbonate to be added, is not particularly limited so long as it is an amount sufficient to precipitate the alkali metal or alkaline earth metal carbonate.

By this first reactive crystallization step, from the alkali metal or alkaline earth metal salt of organic acid A, an alkali metal or alkaline earth metal carbonate will precipitate, and an ammonium salt of organic acid A will form. From the ammonium salt of organic acid A formed in the first reactive crystallization step, in the next second reactive crystallization step, organic acid A can be precipitated by reactive crystallization by means of acid B in the same manner as in the reactive crystallization step in the case where the above-mentioned ammonia type neutralizing agent is employed.

Separation, Recovery and Recycling of Acid B, Organic Acid A and Ammonium Salts Thereof in the Separated Mother Liquor The separated mother liquor (hereinafter sometimes referred to as "the crystallization mother liquor" or "the mother liquor") after separating organic acid A from the reactive crystallization solution, contains an ammonium salt of organic acid A, an ammonium salt of acid B formed by an acid/base reaction therewith, excess acid B and residual organic acid A. In the present invention, acid B and its ammonium salt are efficiently separated from such a separated mother liquor by the following method, whereby the ammonium salt of organic acid A, and organic acid A, can be recovered. Further, the separated ammonium salt of acid B is decomposed, and acid B and ammonia thereby obtained, are reused.

In the present invention, firstly, acid B is vaporized and removed from the crystallization mother liquor, followed by further heating to vaporize the ammonium salt of acid B. The vaporization of acid B from the crystallization mother liquor is preferably carried out at a temperature of not higher than the melting point of the ammonium salt of acid B, and it can be carried out by means of e.g. a kettle type evaporator, a thin film evaporator, a flashed drum having a heating section, a combination of a heat exchanger and a flash drum, or a combination thereof. In a case where one having a distillation column form is employed, if the interior of the column is not higher than the melting point of the ammonium salt of acid B, the crystallization mother liquor may be supplied to any position, such as a condenser section, a reflux line, etc. The specification and the form of the apparatus may be any so long as they are under such a condition that acid B can be vaporized at a temperature of not higher than the melting point of the ammonium salt of acid B.

The temperature range for vaporization of acid B is preferably at least 20° C. and at most the melting point of the ammonium salt of acid B. The melting point of ammonium acetate as a typical example of the ammonium salt of acid B in the present invention, is 114° C. The melting point has a specific meaning in the motion of the molecule, and if ammonium acetate exceeds the melting point, it will be vaporized while being pyrolized. A boiling point of the ammonium salt of acid B is theoretically necessarily present, and a phenomenon such as sublimation is also involved. It is difficult to strictly divide one due to the pyrolysis and contribution of evaporation or sublimation. Accordingly, vaporization of the ammonium salt of acid B may sometimes be called as "decomposition/vaporization" in the present invention, On the other hand, ammonium propionate has strong deliquescence, and its melting point is not known. However, taking into consideration the similarity to ammonium acetate, it is difficult to simply consider that the difference in the melting point between acetic acid and propionic acid will be the difference in the melting point of their ammonium salts. However, a temperature slightly lower than 114° C., i.e. about 100° C., is assumed to be the melting point of ammonium propionate.

Melting point of acetic acid: 16.6° C.
Melting point of ammonium acetate: 114° C.
Melting point of propionic acid: −20.8° C.

Thus, the temperature for vaporization of acid B varies also depending upon the type of acid B (i.e. the type of the ammonium salt of acid B), but it is usually preferably within a range of from 40 to 100° C. At the time of vaporizing acid B at such a temperature, the operation conditions other than the temperature are not particularly limited. However, with respect to the pressure condition, reduced pressure or atmospheric pressure is preferred, since corrosion of the material of the apparatus will be vigorous if the pressure is elevated. Particularly preferred is a reduced pressure condition of from 10 to 400 mmHg, more preferably, from 40 to 200 mmHg.

At the time of vaporization of such acid B, substances having melting points lower than acid B contained in the crystallization mother liquor, such as water, etc., will also be vaporized.

Thus, acid B in the crystallization mother liquor is vaporized and recovered, but from the viewpoint of the subsequent operations, i.e. vaporization of the ammonium salt of acid B, recovery of the residual ammonium salt of organic acid A, or organic acid A, etc., the amount of acid B to be vaporized and removed from the crystallization mother liquor may vary also depending upon the amounts of acid B and other components in the crystallization mother liquor, but the degree of vaporization may be to such an extent that the mother liquor will be a slurry. If the vaporization is proceeded to obtain solid, in a usual method by the second vaporization apparatus, the thermal conductivity tends to deteriorate (e.g. a thin film evaporator), such being undesirable. As an index, the solubility of organic acid A will be saturated at the temperature for vaporization. The saturated solubility is determined by the amount of the ammonium salt of acid B corresponding to the amount of ammonia to be removed and the dissolved amount of organic acid A. In the following, the crystallization mother liquor after vaporizing acid B will sometimes be referred to as "the first residual liquid".

At the time of vaporization of the ammonium salt of acid B after vaporizing acid B, the retention time will be important. Namely, as will be evident from the results of the Test Examples given hereinafter, the amidation reaction will be rapidly accelerated by heating at a temperature of about 120° C. On the other hand, in order to separate the ammonium salt of acid B from organic acid A and its ammonium salt, a higher temperature is required, and a temperature of at least the melting point of the ammonium salt of acid B is particularly preferred.

Accordingly, as a method for vaporizing the ammonium salt of acid B, one having a short heating time is preferred in order to prevent a side reaction such as amidation under such a high temperature condition. Further, it is preferred to carry out the vaporization in a super heated state, i.e. to set the process fluid under a reduced pressure condition, to heat it with a heat source having a sufficiently high temperature. As such a heat source, steam or heating oil may, for example, be usually considered. In such a case, the heating temperature is considered to be preferably at most 200° C., taking into consideration e.g. corrosion by acid B. Otherwise, the temperature may be raised rapidly, for example, by imparting molecular vibration by means of electromagnetic waves. However, the heating temperature may be at least the melting point, and the retention time may not have the upper limit, so long as it is sufficiently short.

Accordingly, with respect to the process fluid, the operable range is at least 0.001 mmHg (0.133 Pa) and at most 200 mmHg (26.7 kPa), more preferably at most 100 mmHg (13.3 kPa). More preferably, it is from 20 mmHg (2.67 kPa) to 90 mmHg (12.0 kPa).

As an apparatus satisfying such a condition, a thin film evaporator may be mentioned which is usually suitable for heating under reduced pressure for a short period of time. Further, a heater having a spraying function or an evaporator having a temperature difference between a utility and the process fluid of at least 20° C., may, for example, be mentioned. The heating method is not particularly limited, and it may be a rapidly heating method by imparting molecular vibration by means of electromagnetic waves in the same principle as for a microwave oven. Any other operation may be employed so long as it satisfies the reduced pressure condition and the high temperature condition, and there is no particular restriction as to the apparatus, the principle or its structure, so long as the heating time is short, and a sufficient heat can be provided.

The heating temperature may vary also depending upon the type of the ammonium salt of acid B or the pressure condition. However, in the case of ammonium acetate, it is preferably from 115 to 180° C., more preferably from 120 to 160° C., and in the case of ammonium propionate, it is preferably from 100 to 180° C.

The liquid or slurry (hereinafter sometimes referred to as "the second residual liquid") obtained by vaporizing the ammonium salt of acid B from the first residual liquid in such a manner, contains organic acid A and its ammonium salt, and residual acid B and its ammonium salt, and it may be circulated to and treated in the reactive crystallization step to further recover organic acid A.

In the present invention, acid B separated by vaporization from the crystallization mother liquor after precipitating and separating organic acid A in the reactive crystallization of the ammonium salt of organic acid A and acid B, is preferably recycled to and reused in the reactive crystallization step. This acid B may contain water and other substances. Recovered acid B is usually purified and then reused as a solvent for crystallization. However, depending upon the type and amount of the impurity, it may be used as it is as a solvent for crystallization without carrying out the purification.

Decomposition of the Ammonium Salt of Acid B

The ammonium salt of acid B separated by vaporization from the crystallization mother liquor, is decomposed into acid B and ammonia. The method for decomposing the ammonium salt of acid B will be described below, but it is not limited to the ammonium salt of acid B obtained from the separated mother liquor of organic acid A, and it is similarly applicable to an ammonium salt of acid B obtained from another process.

In the method for decomposing the ammonium salt of acid B in the present invention, in a heating step, a liquid containing the ammonium salt of acid B, an alkali metal or alkaline earth metal, and water, preferably a liquid having an alkali metal or alkaline earth metal salt of acid B added to a mixed liquid comprising the ammonium salt of acid B and water (hereinafter sometimes referred to as "feed material liquid") is heated to withdraw a gas of a basic aqueous solution. Hereinafter, this step of heating will be referred to as "the heating step", and the operation at that time may sometimes be referred to as "the heating operation".

When the temperature of the gas of a basic aqueous solution withdrawn in the heating step is higher than the melting point of the ammonium salt of acid B, acid B may partially be withdrawn together. Therefore, the withdrawn gas of a basic aqueous solution is subjected to gas/liquid separation, gas/solid separation or gas/liquid/solid separation of the ammonium salt of acid B at a temperature of not higher than the melting point of the ammonium salt of acid B under reduced pressure or atmospheric pressure, directly or after condensation. This separating step will be hereinafter referred to as "the separation step", and its operation may sometimes be referred to as "the separating operation".

The alkali metal and/or alkaline earth metal to form the alkali metal salt and/or alkaline earth metal salt of acid B is preferably at least one member selected from the group consisting of Na, K, Ca and Mg. Particularly preferred is Na or K.

The apparatus to be used for this heating step may be any apparatus so long as it is one capable of heating operation and capable of separating a gas phase and a liquid phase. The heating and the gas/liquid separation may be carried out in separate apparatus or by a combination of a heat exchanger and a flash drum. In the case of a kettle type heat exchanger, the heating and the gas/liquid separation can be carried out in one apparatus. Further, the heating mechanism is not particularly limited, and it may, for example, be a flash drum provided with a jacket or a heat conductive coil.

In order to carry out both the heating and the gas/liquid separation efficiently, a distillation column is most preferred. The distillation column may be either a packed column or a plate column, and there is no particular restriction also with respect to the structure. However, to secure the retention time as described hereinafter, a plate column is preferred. Further, the reboiler may be built-in or externally attached. When an external reboiler is employed, it may be a forcibly circulating type reboiler, a thermo-siphon type reboiler or a kettle type reboiler, but it is not limited thereto. In the present invention, an operation carried out by a combination of a distillation column and a reboiler, is regarded as a heating operation.

There is no restriction as to the presence or absence of a condenser, and a condenser is not one which constitutes a part of the heating operation. Theoretically, a kettle type heat exchanger or a flash drum equipped with a heating device may be regarded as a single plate distillation column.

The gas withdrawn in the heating step, contains ammonia and necessarily has a pH of higher than 7. Accordingly, in this invention, this is referred to as the heating step for withdrawing a gas of a basic aqueous solution.

Among apparatus to carry out such a heating operation to withdraw the gas of such a basic aqueous solution, most preferred is a distillation column. Accordingly, the following description will be made with respect to a case where a distillation column is mainly employed.

In order to obtain the effect for separating acid B and water by a salt effect and at the same time to decompose the ammonium salt of acid B, a distillation column is suitable. Ammonia is considered to be not in usual gas/liquid equilibrium (evaporation and condensation are in the same amount) but be substantially influenced by the retention time and the size of the gas/liquid interface area, and accordingly, in order to carry out the heating step more efficiently, secure hold up of the liquid or a longer retention time becomes important. For this purpose, as the distillation column, a plate (tray) column is preferred. Even with a packed column, hold up of a liquid may be obtained to some extent, but with a plate (tray) column rather than a packed column, the effect for separating acid B and water by a salt effect, and the effect for decomposing the ammonia salt of acid B can be simultaneously obtained more certainly.

With respect to the tray type of the plate column, when the operation range at the time of the start up or shut down is taken into consideration, a sieve tray is practically inferior, as weeping is likely to take place. Even if the operation rate is low or 0, a tray whereby a liquid is certainly held on the tray and weeping scarcely occurs, is preferred. As such a tray, a bubble tray may be mentioned as one example of a fixed tray. With a bubble tray, in order to improve the gas/liquid contact on the tray, in addition to a weir for downcomer, a weir is present also at gas holes on the tray from the construction of the bubble portion, whereby the depth of liquid can be maintained. Further, like a valve cap tray, a tray of the type wherein holes on the tray may be closed by a movable cap, scarcely undergoes weeping and is thus preferably applied to the present invention.

However, when the temperature profile in the interior of the column is taken into consideration, if the temperature becomes high in a state where water is little, amidation take place, and therefore, it is preferred to shorten the retention time at the lower portion of the column where stripping of water is carried out. Therefore, it is preferred that the upper portion of the column is a plate column, and the lower portion is a packed column. Their ratio or the plate number varies depending upon the temperature or the pressure and may suitably be optimized.

In order to obtain the effect for separating acid B and water by a salt effect by the entire apparatus, in the case of a distillation column, it is preferred to supply the feed material from the top of the column, i.e. to carry out the separation in the form of so-called extraction distillation. However, the plate where the feed material is supplied is not particularly limited.

The pressure of the column is not particularly limited, but for efficient decomposition of the ammonium salt of acid B, it must be a pressure such that at least the column bottom temperature will be at least 80° C., preferably from 115 to 180° C. Further, if the column top is at a temperature lower than whichever is higher between the melting point of the ammonium salt of acid B and the boiling point of acid B, the column top portion can be regarded as a gas/liquid separation apparatus in the separation step after the heating step, whereby it becomes possible to carry out the heating step and the separation step in one apparatus, and the number of apparatus can be reduced, such being desirable from the viewpoint of the investment cost. The temperature condition at the column top in such a case is not higher than 114° C. (the melting point of ammonium acetate) in a case where the ammonium salt of acid B is ammonium acetate, or not higher than 141° C. (the boiling point of propionic acid) in the case of ammonium propionate.

The pressure condition to satisfy the conditions of the column top varies depending upon e.g. the type and the amount of acid B or the alkali metal or alkaline earth metal, the amount of water and the desired degree for separation of water/acid B, but it is usually at most 2.0 atm (0.2 MPa), preferably at most atmospheric pressure (1 atm (0.1 MPa)).

Further, the pressure condition satisfying the conditions of the above-mentioned column bottom likewise varies depending upon e.g. the type and the amount of acid B or the alkali metal or alkaline earth metal, the amount of water, the desired degree for separation of water/acid B, and the pressure loss due to trays or packing material, but it is usually at least 80 mmHg (10.6 kPa), preferably at least 200 mmHg (26.7 kPa).

When the feed material is supplied to the column top portion, acid B or its salt may sometimes be distilled off by a stripping effect or entrainment (inclusion of splash). In such a case, even if the conditions for the heating operation and the separating operation can be satisfied solely by a distillation column, it may be necessary to take some measure such as to lower the supply plate or to additionally install a gas/liquid separation apparatus corresponding to the separating operation for the purpose of removing the salt by stripping.

Whereas, in a case where a distillation column as one of heating apparatus and a gas/liquid separating apparatus are separated, the gas of a basic aqueous solution withdrawn from the column top of the distillation column may once be condensed by a condenser and then supplied to a gas/liquid, gas/liquid/solid or gas/solid separating apparatus. Otherwise, as the case requires, a pressure adjustor may be installed in the withdrawing line from the column top, so that the condenser may be made to be a gas/liquid, gas/liquid/solid or gas/solid separating apparatus. In the former case, the supply to the gas/liquid separating apparatus will be mainly a liquid, but it may be supplied as gas/liquid. In the latter case, the supply to the gas/liquid separating apparatus may accompany entrainment (inclusion of splash) but is mostly a gas.

The liquid, solid or slurry withdrawn from the gas/liquid, gas/liquid/solid or gas/solid separating apparatus, is mainly one having the ammonium salt of acid B distilled by the stripping effect, concentrated. This concentrate may be returned to the heating apparatus to carry out the heating step, or mixed to an aqueous solution of an ammonium salt of acid B to be supplied afresh, or to an aqueous solution of acid B, and subjected to recycling treatment until it is decomposed.

Either in a case where the distillation column for the heating step and the gas/liquid, gas/liquid/solid or gas/solid separating apparatus for the separation step are unitary or in a case where they are separate apparatus, the liquid withdrawn from the bottom of the column is separated into acid B and the alkali metal or alkaline earth metal salt of acid B by a usual method such as one by means of an evaporator or a thin film evaporator. Otherwise, gas withdrawal may be carried out from a recovery portion (a recovery plate) of the distillation column as a heater.

Having been subjected to a heat history by the process up to this stage, the ammonium salt of acid B has been partially amidated. Such an amide compound has a high boiling point, and the majority takes a behavior similar to an alkali metal or alkaline earth metal salt of acid B. The boiling point of acetamide as a typical amide compound is 222° C. and will not substantially be included. Even if such an amide compound is included slightly in acid B, for example, by entrainment, it can readily be separated by a usual method such as distillation.

Such an amide compound will be hydrolyzed by the presence of an alkali metal or an alkaline earth metal, when water is added, followed by heating. Namely, the alkali metal or alkaline earth metal salt of acid B is recovered for recycling, and before it is supplied to a heating step i.e. to a heating apparatus provided separately from a separating apparatus or to a distillation column as a heating apparatus, or to a distillation apparatus, as mixed to an aqueous solution of an ammonium salt of acid B or an aqueous solution of acid B to be supplied afresh, it may be preheated, or it may be heated in the heating apparatus or the distillation apparatus, whereby the amide compound can be hydrolyzed and removed.

In the present invention, the type of the alkali metal or alkaline earth metal is not particularly restricted, and one type may be used alone, or two or more types may be used in combination. As between the alkali metal and the alkaline earth metal, the alkaline earth metal is likely to take a crosslinked structure and thus has a drawback such that it is likely to bring about a problem of high viscosity or crystallization. Accordingly, an alkali metal is preferred. Among alkali metals, sodium or potassium is particularly preferred in a case where the product to which this process is applied, is a food additive or a pharmaceutical, or when economical efficiency or handling efficiency is taken into consideration. Further, they may be used as mixed.

The ammonium salt of acid B is heated at a temperature of at least 80° C., preferably from 100 to 160° C., under a condition of at least pH 6.5, preferably from pH 7 to pH 10 together with an alkali metal salt (such as a sodium salt or a potassium salt) and/or an alkaline earth metal salt (such as a magnesium salt or a calcium salt) of acid B in the presence of a proper amount e.g. from 0.3 to 10 times by weight, preferably from 0.5 to 5 times by weight, to the ammonium salt of acid B, of water, whereby ammonia can be vaporized.

Especially when a reactive distillation apparatus is employed, the column top portion is at least pH 7, and the column bottom portion is at most pH 7. With respect to such conditions, the ammonium salt of acid B can be decomposed by using from 0.3 to 5 times by weight, preferably from 0.5 to 3 times by weight, of water, and from 0.2 to 2 times by weight, preferably from 0.5 to 1.5 times by weight, of an alkali metal salt (such as a sodium salt or a potassium salt) and/or an alkaline earth metal salt (such as a magnesium salt or a calcium salt) of acid B, to the ammonium salt of acid B.

The smaller the amount of water, the smaller the consumption of energy, but amidation is more likely to take place. Accordingly, it is suitably controlled depending upon the type of acid B, the type and amount of the alkali metal or alkaline earth metal, the structure of the apparatus, the retention time distribution, etc.

Further, the method of the present invention can be used also as an economically effective method for separating an industrially important aqueous acetic acid solution, by mixing ammonia to e.g. an aqueous acetic acid solution to obtain an aqueous ammonium acetate solution. In such a case, the withdrawn aqueous ammonia or a vapor containing ammonia is separated into pure water and concentrated aqueous ammonia by a usual method such as distillation, and the concentrated aqueous ammonia or ammonia gas is returned to an aqueous acetic acid solution to be supplied afresh and recycled for use. Thus, this method is particularly effective for purification of water having a small acetic acid content.

Further, in the present invention, the liquid after withdrawing the gas of a basic aqueous solution in the heating step, contains mainly free acid B obtained by decomposition of the alkali metal or alkaline earth metal salt of acid B and a non-decomposed ammonium salt of acid B. This liquid may be heated under reduced pressure or atmospheric pressure, preferably under reduced pressure, more preferably at most 100 mmHg, particularly preferably at most 75 mmHg at a temperature of at least 125° C., preferably at least 135° C., more preferably at least 160° C., particularly preferably from 180 to 220° C., whereby acid B can be separated and recovered. Acid B thus recovered, can be reused in the above-mentioned reactive crystallization step. If the operation is carried out under sufficiently reduced pressure (at most 100 mmHg) at a high temperature (at least 180° C.), an acid B amide compound and the non-reacted ammonium salt of acid B will be vaporized together with acid B. They are separated by a usual method (such as distillation), whereby acid B having a higher purity can be obtained.

Further, the residue after separating and recovering acid B as described above, contains an alkali metal or alkaline earth metal, a non-decomposed ammonium salt of acid B, and an amide compound of acid B as a byproduct, and such residue can be recycled for use as an alkali metal or alkaline earth metal source. In such a case, this residue contains an amide compound of acid B as a byproduct. This amide compound can easily be hydrolyzed in the presence of an alkali metal and water. After adding water or a liquid containing acid B and water to the above residue, the amide compound of acid B as a byproduct, can be hydrolyzed at a temperature of at least 125° C., preferably at least 140° C., more preferably at least 150° C.

Now, with reference to the drawings, specific constructions of apparatus suitable for carrying out the method for decomposing the ammonium salt of acid B, will be described. However, it should be understood that the present invention is by no means restricted to the methods shown in the drawings. Further, in the following, ammonium acetate is exemplified as an ammonium salt of acid B, and sodium is exemplified as an alkali metal or alkaline earth metal. However, it is needless to say that the present invention is not limited to ammonium acetate and sodium, but is applicable to other ammonium salts of acid B and other alkali metals or alkaline earth metals.

In the method of FIG. 1, ammonium acetate and water are supplied to a distillation column 1 via an acetamide decomposition vessel 3. To this acetamide decomposition vessel 3, a residue (containing sodium acetate, acetamide as byproduct and non-decomposed ammonium acetate) from a thin film evaporator 4 of a later stage, is recycled, and this residue is mixed with an aqueous ammonium acetate solution and sent to the distillation column 1 and introduced to the upper portion of the distillation column 1. As mentioned above, in this acetamide decomposition vessel 3, acetamide is mixed with water, whereby hydrolysis of acetamide is carried out.

The mixed liquid from the acetamide decomposition vessel 3 is subjected to the heating operation and the separating operation under the above-described distillation conditions in the distillation column 1, whereby a gas of a basic aqueous solution containing ammonia, water and a small amount of ammonium acetate, will be distilled from the top of the distillation column 1. This gas of a basic aqueous solution is subjected to gas/liquid separation at a temperature of not higher than the melting point of ammonium acetate in a vaporizer 2, whereby water and ammonia are separated. Residual ammonium acetate is supplied to the acetamide decomposition vessel 3 and subjected to recycling treatment.

The bottom liquid from the bottom of the distillation column 1, contains acetic acid, non-decomposed ammonium acetate, acetamide as a byproduct and sodium acetate. In a thin film evaporator 4, acetic acid is separated, and the residue is recycled to the acetamide decomposition vessel 3.

Figure 2:
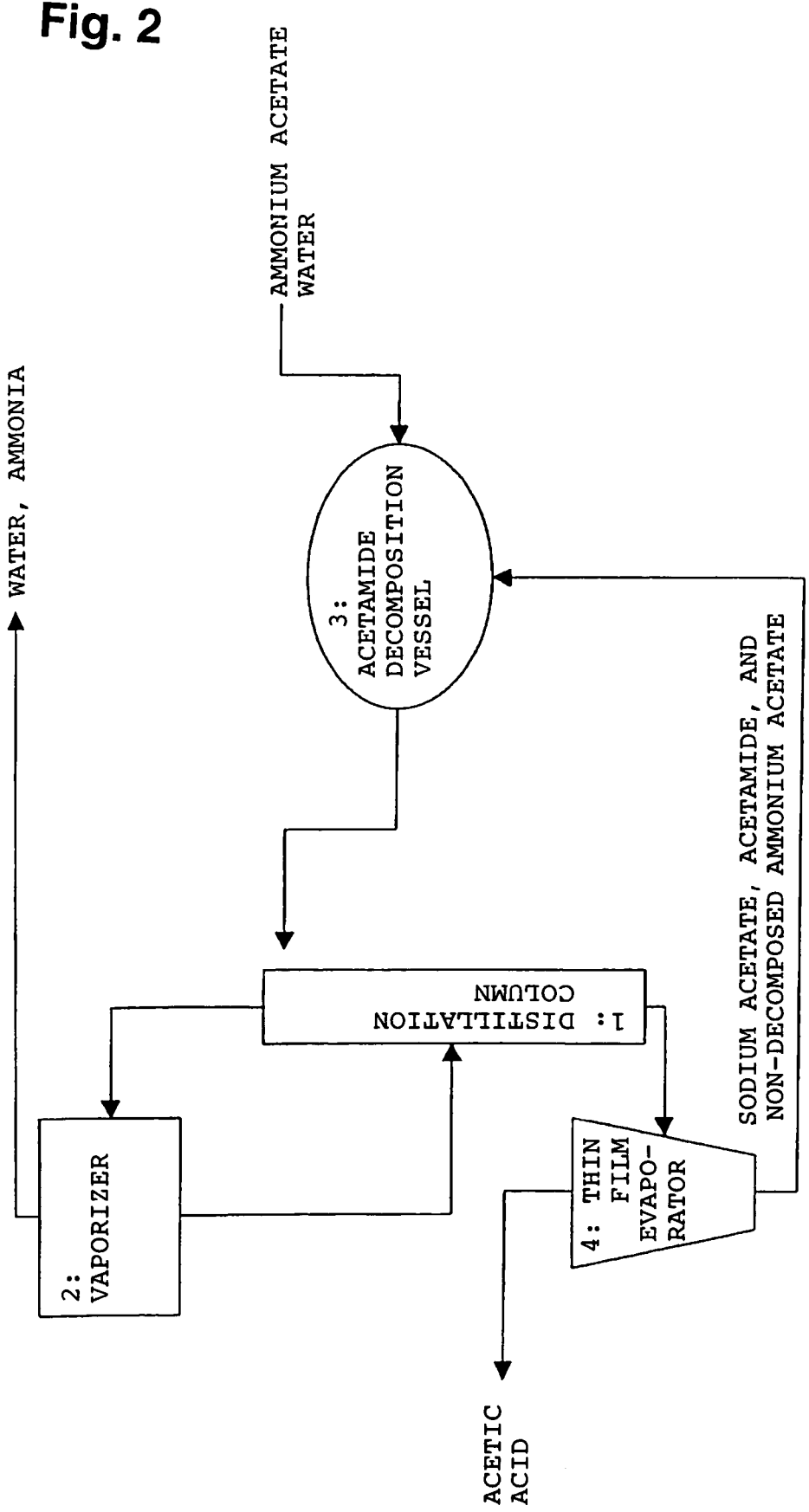
FIG. 2 is a schematic flowchart showing the construction of another apparatus suitable for carrying out the method for decomposition of an ammonium salt of acid B of the present invention.

The method shown in FIG. 2, is different from the method shown in FIG. 1 in that the ammonium acetate distillate from the vaporizer 2 is returned to the distillation column 1, but the heating operation and the separating operation are carried out in the same manner as in FIG. 1.

Figure 3:
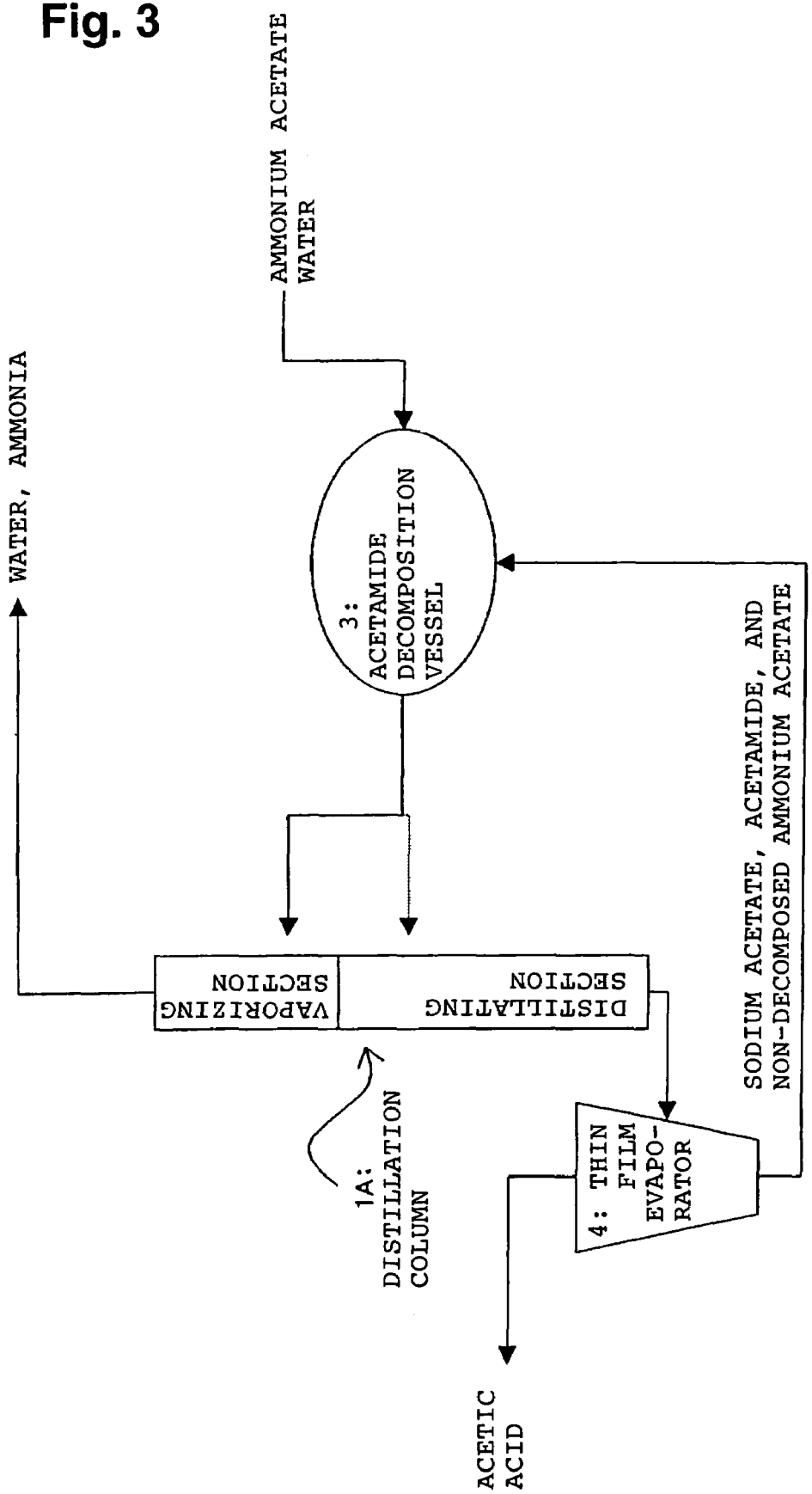
FIG. 3 is a schematic flowchart showing the construction of another apparatus suitable for carrying out the method for decomposition of an ammonium salt of acid B of the present invention.

The method shown in FIG. 3 is different from the method shown in FIG. 1 in that in the distillation column 1A, vaporization and distillation are carried out to omit the vaporizer 2, but the heating operation and the separating operation are carried out in the same manner as in FIG. 1. Further, in this method, the mixed liquid from the acetamide decomposition vessel 3 may be introduced to the vaporizing section or to the upper portion of the distilling section in the distillation column 1A.

Figure 4:
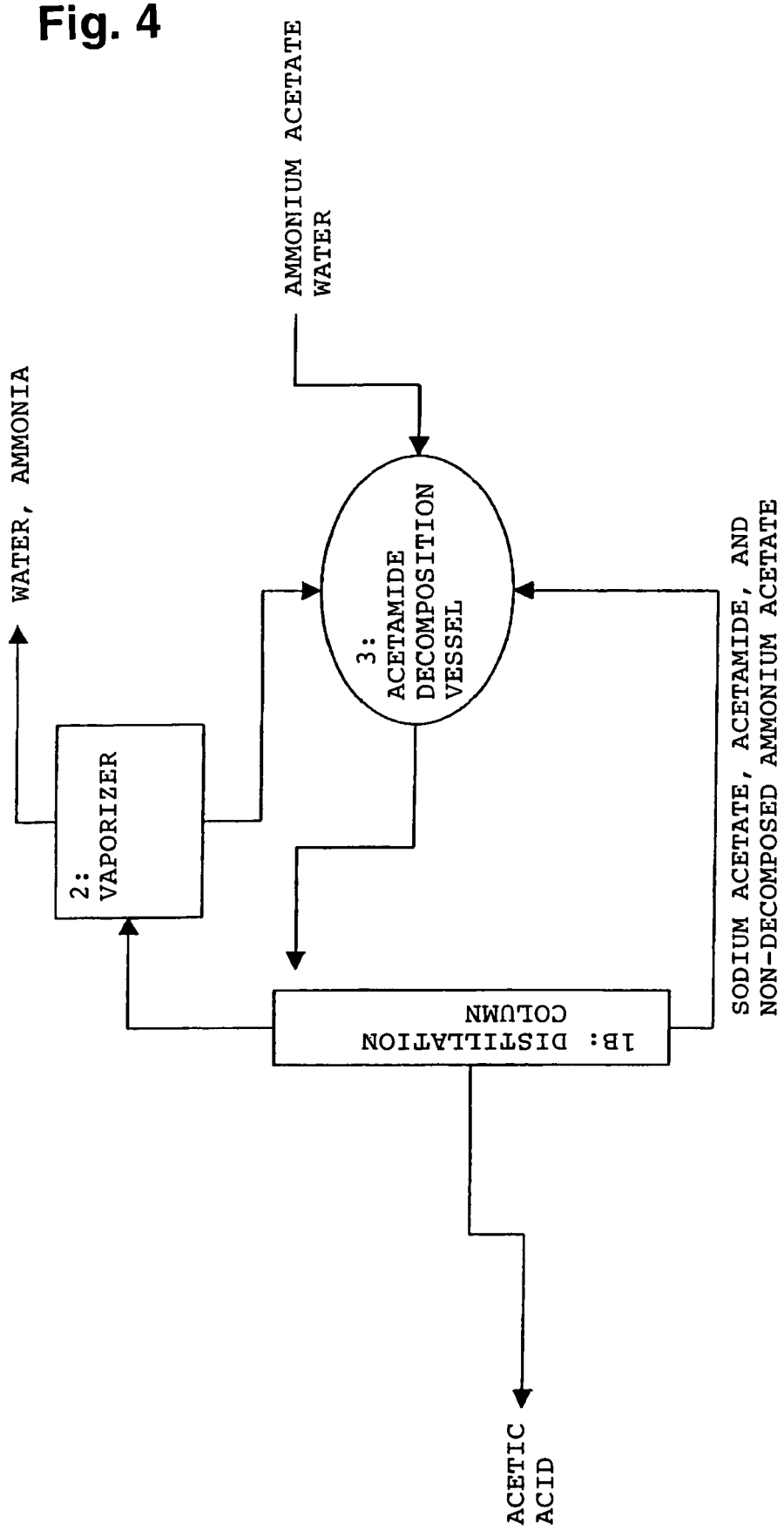
FIG. 4 is a schematic flowchart showing the construction of another apparatus suitable for carrying out the method for decomposition of an ammonium salt of acid B of the present invention.

The method shown in FIG. 4 is different from the method shown in FIG. 1 in that in the distillation column 1B, acetic acid is withdrawn from an intermediate plate to carry out also separation of acetic acid thereby to omit a thin film evaporator 4, but the heating and separating operations are carried out in the same manner as in FIG. 1.

Figure 5:
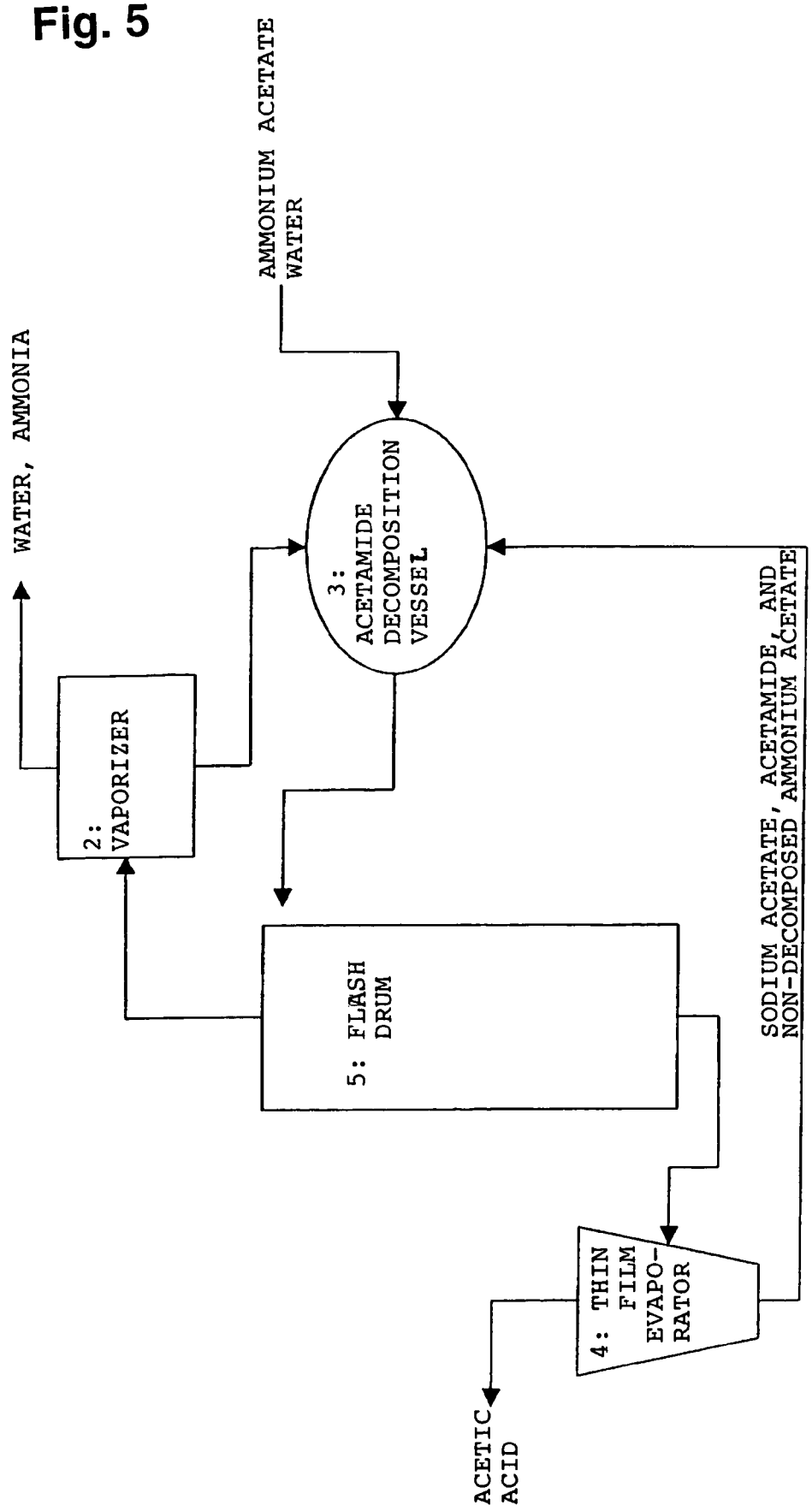
FIG. 5 is a schematic flowchart showing the construction of another apparatus suitable for carrying out the method for decomposition of an ammonium salt of acid B of the present invention.

The method shown in FIG. 5 is different from the method shown in FIG. 1 in that a flash drum 5 is employed instead of the distillation column, but the heating and separating operations are carried out in the same manner as in FIG. 1.

In any one of these methods, by the presence of an alkali metal or an alkaline earth metal, and ammonia, in the heating step such as in the distillation column or flash drum, the reflux ratio will be small, and it is possible to substantially reduce the energy consumed in the heating and separating operations.

Recycling of Separated Mother Liquor

In the present invention, in a case where the reactive crystallization is carried out in multi stages, a mother liquor in a later stage reactive crystallization is mixed with an ammonium salt of organic acid A to be supplied afresh, as a recycling liquid as shown in the following (1) to (3).

(1) The later stage mother liquor is recycled as it is and mixed with an ammonium salt of organic acid A to be supplied afresh. In this later stage mother liquor, acid B and its ammonium salt, and organic acid A and its ammonium salt, are contained. Among them, acid B will be reacted with the ammonium salt of organic acid A to be supplied, thereby to be converted to an ammonium salt of acid B and to precipitate organic acid A monoammonium salt, and in the next vaporization step, it will be removed together with the ammonium salt of acid B in the later stage mother liquor. Whereas, organic acid A and its ammonium salt will be separated as organic acid A and/or its monoammonium salt in the reactive crystallization together with the ammonium salt of organic acid A to be supplied afresh.

(2) From the later stage mother liquor, acid B is vaporized, separated and recovered, and then the residue is recycled and mixed with an ammonium salt of organic acid A to be supplied afresh.

In this case, it is preferable to retain acid B in the residue to such an extent that the residue after vaporization and separation will maintain a liquid phase. Namely, it is necessary that in the recycled liquid, acid B is present in such an amount that the ammonium salt of acid B, organic acid A and its ammonium salt can sufficiently be dissolved therein.

Also in this case, as in the case of (1), acid B in the recycled liquid will be reacted with the ammonium salt of organic acid A to be supplied afresh, and converted to an ammonium salt of acid B, which will be removed in the next vaporization step together with the ammonium salt of acid B in the later stage mother liquor. Whereas, organic acid A and its ammonium salt are separated as organic acid A and/or its monoammonium salt in the reactive crystallization together with an ammonium salt of organic acid A to be supplied afresh.

(3) From the separated mother liquor, acid B is vaporized, separated and recovered, and then the ammonium salt of acid B is vaporized and separated from organic acid A and its ammonium salt, and the distillate of the ammonium salt of acid B is recycled and mixed with an ammonium salt of organic acid A to be supplied afresh.

In this case, it is necessary that in the distillate of the ammonium salt of acid B, acid B is contained to such an extent that this distillate will maintain a liquid phase. Namely, it is necessary that in the recycled liquid, acid B is present in such an amount that the ammonium salt of acid B can sufficiently be dissolved therein.

Also in this case, as in the case of (1), acid B in the recycled liquid, will be reacted with an ammonium salt of organic acid A to be supplied afresh, and converted to an ammonium salt of acid B, which will be removed in the next vaporization step together with the ammonium salt of acid B in the crystallization mother liquor.

Further, the condition for vaporizing acid B from the crystallization mother liquor, is the same as in the case of the above (2). Further, to vaporize the ammonium salt of acid B to separate it from organic acid A and its ammonium salt, it is preferred to employ the same operational condition as in the after-mentioned vaporization step. Organic acid A and its ammonium salt separated by this method, are recycled and treated in the reactive crystallization step to recover organic acid A. The condition for mixing the recycled liquid of the above (1) to (3) with the ammonium salt of organic acid A to be supplied afresh, is not particularly limited, the mixing can be carried out by stirring in a mixing vessel at a temperature of from 20 to 140° C., preferably from 40 to 110° C.

Applications of Organic Acid A

Organic acid A as the desired product obtained by the method of the present invention is useful for various applications. Among them, dicarboxylic acids are useful as raw materials for polyesters or polyamides.

For example, oxalic acid, succinic acid, itaconic acid, glutaric acid, adipic acid, sebacic acid, dodecanoic acid, or lower alcohol esters thereof, succinic anhydride, adipic anhydride, etc., as dicarboxylic acids to be produced by the present invention, are raw materials for high molecular weight polyesters. Particularly from the aspect of the physical properties of the polymer, succinic acid, adipic acid, sebacic acid or an anhydride thereof, is preferred, and such an acid can be produced by the present invention without giving a burden to the environment by a microbial fermentation method from a natural carbon source.

Further, a diol to be used for e.g. production of a polyester copolymer, such as 1,4-butanediol, 1,5-pentanediol, 1,6-hexanediol, 1,4-cyclohexanediol or 1,6-cyclohexanedimethanol, may also be obtained by hydrogenating the above-mentioned organic acid A produced by the present invention.

Specific Preferred Embodiments

Specific preferred embodiments of the present invention are as follows.

1. A method for producing a dicarboxylic acid and/or tricarboxylic acid by bioconversion of a carbon source, which comprises:
   a bioconversion step in which a carbon source is converted by a microorganism in the presence of at least one neutralizing agent selected from the group consisting of ammonia, ammonium carbonate and urea, to obtain a reaction solution containing an ammonium salt of a dicarboxylic acid and/or tricarboxylic acid;

a reactive crystallization step in which reactive crystallization is carried out by adding a monocarboxylic acid to the ammonium salt of a dicarboxylic acid and/or tricarboxylic acid obtained in the bioconversion step, to precipitate the desired dicarboxylic acid and/or tricarboxylic acid; and a separation step in which the dicarboxylic acid and/or tricarboxylic acid precipitated in the reactive crystallization step, is separated.

2. The method for producing a dicarboxylic acid and/or tricarboxylic acid according to Item 1, which includes a concentration step of concentrating the reaction solution obtained in the bioconversion step, and wherein the concentrate obtained in the concentration step is supplied to the reactive crystallization step.

3. The method for producing a dicarboxylic acid and/or tricarboxylic acid according to Item 1 or 2, which includes an ammonia recovery step in which the monocarboxylic acid is vaporized and removed from the liquid after separating the dicarboxylic acid and/or tricarboxylic acid in the separation step, then an ammonium salt of the monocarboxylic acid in the liquid is vaporized and collected, the ammonium salt of the monocarboxylic acid is mixed with water and an alkali metal and/or alkaline earth metal salt of the monocarboxylic acid, followed by heating to vaporize and recover ammonia; and a recycling step in which the ammonia recovered in the ammonia recovery step, is used as a neutralizing agent in the above bioconversion step.

4. A method for producing a dicarboxylic acid and/or tricarboxylic acid by bioconversion of a carbon source, which comprises:

a bioconversion step in which a carbon source is converted by a microorganism in the presence of at least one neutralizing agent selected from the group consisting of an alkali metal hydroxide, an alkaline earth metal hydroxide, an alkali metal carbonate and an alkaline earth metal carbonate, to obtain a reaction solution containing an alkali metal and/or alkaline earth metal salt of a dicarboxylic acid and/or tricarboxylic acid;

a first reactive crystallization step in which reactive crystallization is carried out by adding ammonia and carbon dioxide, and/or ammonium carbonate, to the alkali metal and/or alkaline earth metal salt of a dicarboxylic acid and/or tricarboxylic acid obtained in the bioconversion step, to precipitate a carbonate of the alkali metal and/or alkaline earth metal, and the carbonate is separated to obtain an aqueous solution of an ammonium salt of the dicarboxylic acid and/or tricarboxylic acid;

a second reactive crystallization step in which reactive crystallization is carried out by adding a monocarboxylic acid to the liquid after removing the carbonate of the alkali metal and/or alkaline earth metal precipitated in the first reactive crystallization step, to precipitate the desired dicarboxylic acid and/or tricarboxylic acid; and a separation step in which the dicarboxylic acid and/or tricarboxylic acid precipitated in the second reactive crystallization step, is separated.

5. The method for producing a dicarboxylic acid and/or tricarboxylic acid according to Item 4, which includes a concentration step of concentrating the reaction solution obtained in the bioconversion step, and wherein the concentrate obtained in the concentration step is supplied to the first reactive crystallization step.

6. The method for producing a dicarboxylic acid and/or tricarboxylic acid according to Item 4 or 5, which includes an ammonia recovery step in which the monocarboxylic acid is vaporized and removed from the liquid after separating the dicarboxylic acid and/or tricarboxylic acid in the separation step, then an ammonium salt of the monocarboxylic acid in the liquid is vaporized and collected, the ammonium salt of the monocarboxylic acid is mixed with water and an alkali metal and/or alkaline earth metal salt of the monocarboxylic acid, followed by heating to vaporize and recover ammonia; and a recycling step in which the ammonia recovered in the ammonia recovery step, is used as an ammonia source in the above first reactive crystallization step.

7. A method for producing a dicarboxylic acid and/or tricarboxylic acid wherein a dicarboxylic acid and/or tricarboxylic acid is obtained from an ammonium salt of a dicarboxylic acid and/or tricarboxylic acid, which comprises:

a reactive crystallization step in which reactive crystallization is carried out by adding a monocarboxylic acid to the ammonium salt of a dicarboxylic acid and/or tricarboxylic acid, to precipitate the dicarboxylic acid and/or tricarboxylic acid;

a separation step in which the dicarboxylic acid and/or tricarboxylic acid precipitated in the reactive crystallization step, is separated;

a step for recovering ammonia and the monocarboxylic acid, in which an ammonium salt of the monocarboxylic acid is separated from the liquid containing the ammonium salt of the monocarboxylic acid after separating the dicarboxylic acid and/or tricarboxylic acid in the separation step, and then, an alkali metal and/or alkaline earth metal salt of the monocarboxylic acid is added to this separated ammonium salt of the monocarboxylic acid to obtain the monocarboxylic acid and ammonia; and a recycling step in which the ammonia and monocarboxylic acid recovered in the step for recovering ammonia and the monocarboxylic acid, are used as an ammonia source for the ammonium salt of the dicarboxylic acid and/or tricarboxylic acid and as the monocarboxylic acid in the above reactive crystallization step, respectively.

8. The method for producing a dicarboxylic acid and/or tricarboxylic acid according to Item 7, wherein the ammonium salt of the dicarboxylic acid and/or tricarboxylic acid is obtained by bioconversion of a carbon source employing, as a neutralizing agent, at least one member selected from the group consisting of ammonia, ammonium carbonate and urea.

9. The method for producing a dicarboxylic acid and/or tricarboxylic acid according to Item 7, wherein the ammonium salt of the dicarboxylic acid and/or tricarboxylic acid, is obtained by a Solvay method in which the ammonium salt of the dicarboxylic acid and/or tricarboxylic acid is obtained from an alkali metal and/or alkaline earth metal salt of the dicarboxylic acid and/or tricarboxylic acid obtained by bioconversion of a carbon source employing, as a neutralizing agent, at least one member selected from the group consisting of an alkali metal hydroxide, an alkaline earth metal hydroxide, an alkali metal carbonate and an alkaline earth metal carbonate.

10. The method for producing a dicarboxylic acid and/or tricarboxylic acid according to any one of Items 1 to 9, wherein the carbon number of the dicarboxylic acid and/or tricarboxylic acid is from 4 to 12.

11. The method for producing a dicarboxylic acid and/or tricarboxylic acid according to Item 10, wherein the dicarboxylic acid and/or tricarboxylic acid is at least one member selected from the group consisting of succinic acid, adipic acid, malic acid, tartaric acid, fumaric acid, maleic acid, citric acid, asparaginic acid and glutamic acid.

12. The method for producing a dicarboxylic acid and/or tricarboxylic acid according to any one of Items 1 to 11, wherein the carbon number of the monocarboxylic acid is from 1 to 6.

13. The method for producing a dicarboxylic acid and/or tricarboxylic acid according to Item 12, wherein the monocarboxylic acid is acetic acid and/or propionic acid.

14. A method for producing a dicarboxylic acid and/or tricarboxylic acid in which a dicarboxylic acid and/or tricarboxylic acid is obtained from an ammonium salt of the dicarboxylic acid and/or tricarboxylic acid, which comprises:

a reactive crystallization step in which reactive crystallization is carried out by adding a monocarboxylic acid to the ammonium salt of the dicarboxylic acid and/or tricarboxylic acid, to precipitate the dicarboxylic acid and/or tricarboxylic acid;

a separation step in which the dicarboxylic acid and/or tricarboxylic acid precipitated in the reactive crystallization step, is separated;

a first vaporization step in which the monocarboxylic acid is further vaporized from the crystallization mother liquor after separating the dicarboxylic acid and/or tricarboxylic acid in the separation step;

a second vaporization step in which an ammonium monocarboxylate is vaporized from the crystallization mother liquor after the first vaporization step.

15. The method for producing a dicarboxylic acid and/or a tricarboxylic acid according to Item 14, wherein the first vaporization step is a step of vaporizing the monocarboxylic acid from the crystallization mother liquor at a temperature of not higher than the melting point of the ammonium monocarboxylate.

16. The method for producing a dicarboxylic acid and/or tricarboxylic acid according to Item 14 or 15, wherein the second vaporization step is a step of vaporizing the ammonium monocarboxylate by heating the above crystallization mother liquor under a reduced pressure of from 0.001 mmHg (0.133 Pa) to 200 mmHg (26.7 kPa).

17. The method for producing a dicarboxylic acid and/or tricarboxylic acid according to any one of Items 14 to 16, in which the carbon number of the dicarboxylic acid and/or tricarboxylic acid is from 4 to 12.

18. The method for producing a dicarboxylic acid and/or tricarboxylic acid according to Item 17, wherein the dicarboxylic acid and/or tricarboxylic acid is at least one member selected from the group consisting of succinic acid, adipic acid, malic acid, tartaric acid, fumaric acid, maleic acid, citric acid, asparaginic acid, glutaric acid and glutamic acid.

19. The method for producing a dicarboxylic acid and/or tricarboxylic acid according to any one of Items 14 to 18, wherein the carbon number of the monocarboxylic acid is from 1 to 6.

20. The method for producing a dicarboxylic acid and/or tricarboxylic acid according to Item 19, wherein the monocarboxylic acid is acetic acid and/or propionic acid.

21. A method for producing a dicarboxylic acid and/or tricarboxylic acid in which a dicarboxylic acid and/or tricarboxylic acid is obtained from an ammonium salt of the dicarboxylic acid and/or tricarboxylic acid, which comprises:

a reactive crystallization step in which reactive crystallization is carried out by adding a monocarboxylic acid to the ammonium salt of the dicarboxylic acid and/or tricarboxylic acid, to precipitate the dicarboxylic acid and/or tricarboxylic acid;

a supplying step in which the ammonium salt of the dicarboxylic acid and/or tricarboxylic acid is supplied to the reactive crystallization step; and a separation step in which the dicarboxylic acid and/or tricarboxylic acid precipitated in the reactive crystallization step, is separated; and which includes:

a recycling step in which the crystallization mother liquor after separating the dicarboxylic acid and/or tricarboxylic acid in the separation step, is recycled to the above supplying step;

a mixing step in which the recycled liquid in the recycling step is mixed with an ammonium salt of the dicarboxylic acid and/or tricarboxylic acid supplied afresh in the supplying step; and a vaporization step in which an ammonium salt of the monocarboxylic acid is vaporized from the mixture obtained in the mixing step, wherein the residue after vaporizing and removing the ammonium salt of the monocarboxylic acid in the vaporization step, is supplied to the above reactive crystallization step.

22. A method for producing a dicarboxylic acid and/or tricarboxylic acid in which a dicarboxylic acid and/or tricarboxylic acid is obtained from an ammonium salt of the dicarboxylic acid and/or tricarboxylic acid, which comprises:

a reactive crystallization step in which reactive crystallization is carried out by adding a monocarboxylic acid to the ammonium salt of the dicarboxylic acid and/or tricarboxylic acid, to precipitate the dicarboxylic acid and/or tricarboxylic acid;

a supplying step in which the ammonium salt of the dicarboxylic acid and/or tricarboxylic acid is supplied to the reactive crystallization step; and a separation step in which the dicarboxylic acid and/or tricarboxylic acid precipitated in the reactive crystallization step, is separated; and which includes:

a monocarboxylic acid recovery step in which the monocarboxylic acid is vaporized and separated from the crystallization mother liquor after separating the dicarboxylic acid and/or tricarboxylic acid in the separation step;

a recycling step in which the residual liquid after removing the monocarboxylic acid in the monocarboxylic acid recovery step, is recycled to the above supplying step;

a mixing step in which the recycled liquid in the recycling step, is mixed with an ammonium salt of the dicarboxylic acid and/or tricarboxylic acid supplied afresh in the supplying step; and a vaporization step in which the ammonium salt of the monocarboxylic acid is vaporized from the mixture obtained in the mixing step, in which a residue after vaporizing and removing the ammonium salt of the monocarboxylic acid in the vaporization step, is supplied to the above reactive crystallization step.

23. A method for producing a dicarboxylic acid and/or tricarboxylic acid in which a dicarboxylic acid and/or tricarboxylic acid is obtained from an ammonium salt of the dicarboxylic acid and/or tricarboxylic acid, which comprises:

a reactive crystallization step in which reactive crystallization is carried out by adding a monocarboxylic acid to the ammonium salt of the dicarboxylic acid and/or tricarboxylic acid, to precipitate the dicarboxylic acid and/or tricarboxylic acid;

a supplying step in which the ammonium salt of the dicarboxylic acid and/or tricarboxylic acid is supplied to the reactive crystallization step; and a separation step in which the dicarboxylic acid and/or tricarboxylic acid precipitated in the reactive crystallization step, is separated, and which includes:

a first recovery step in which the monocarboxylic acid is vaporized and separated from the crystallization mother liquor after separating the dicarboxylic acid and/or tricarboxylic acid in the separation step;

a second recovery step in which the dicarboxylic acid and/or tricarboxylic acid, and its ammonium salt, are separated from the residual liquid after removing the monocarboxylic acid in the first recovery step;

a recycling step in which the residual liquid after separating the dicarboxylic acid and/or tricarboxylic acid, and its ammonium salt in the second recovery step, is recycled to the above supplying step;

a mixing step in which the recycled liquid in the recycling step, is mixed with an ammonium salt of the dicarboxylic acid and/or tricarboxylic acid supplied afresh in the supplying step; and a vaporization step in which the ammonium salt of the monocarboxylic acid is vaporized from the mixture obtained in the mixing step, in which the residue after vaporizing and removing the ammonium salt of the monocarboxylic acid in the vaporization step, is supplied to the above reactive crystallization step.

24. The method for producing a dicarboxylic acid and/or tricarboxylic acid according to any one of Items 21 to 23, wherein the mols of the monocarboxylic acid in the recycled liquid to the mols of the dicarboxylic acid and/or tricarboxylic acid supplied afresh in the above mixing step, are at most 30 times.

25. The method for producing a dicarboxylic acid and/or tricarboxylic acid according to any one of Items 21 to 24, wherein the vaporization step is a step of vaporizing the ammonium salt of the monocarboxylic acid by heating the above mixture under a reduced pressure of from 0.001 mmHg (0.133 Pa) to 200 mmHg (26.7 kPa).

26. The method for producing a dicarboxylic acid and/or tricarboxylic acid according to any one of Items 21 to 25, wherein the carbon number of the dicarboxylic acid and/or tricarboxylic acid is from 4 to 12.

27. The method for producing a dicarboxylic acid and/or tricarboxylic acid according to Item 26, wherein the dicarboxylic acid and/or tricarboxylic acid is at least one member selected from the group consisting of succinic acid, adipic acid, malic acid, tartaric acid, fumaric acid, maleic acid, citric acid, asparaginic acid, glutaric acid and glutamic acid.

28. The method for producing a dicarboxylic acid and/or tricarboxylic acid according to any one of Items 21 to 27, wherein the carbon number of the monocarboxylic acid is from 1 to 6.

29. The method for producing a dicarboxylic acid and/or tricarboxylic acid according to Item 28, wherein the monocarboxylic acid is acetic acid and/or propionic acid.

30. A method for decomposing an ammonium salt of a monocarboxylic acid to separate and recover a monocarboxylic acid and ammonia, which comprises a heating step in which a liquid containing an ammonium salt of a monocarboxylic acid, an alkali metal and/or alkaline earth metal and water, is heated to withdraw a gas of a basic aqueous solution, and a separation step in which the gas of a basic aqueous solution withdrawn from the heating step is, directly or after condensation, subjected to gas/liquid separation, gas/solid separation or gas/liquid/solid separation at a temperature of not higher than the melting point of the ammonium salt of the monocarboxylic acid.

31. The method for decomposing an ammonium salt of a monocarboxylic acid according to Item 30, in which a liquid containing the ammonium salt of a monocarboxylic acid, an alkali metal salt and/or alkaline earth metal salt of the monocarboxylic acid, or ions derived therefrom, and water, is supplied to a distillation column, and the gas of a basic aqueous solution, is withdrawn from the top of the distillation column.

32. The method for decomposing an ammonium salt of a monocarboxylic acid according to Item 30 or 31, wherein the alkali metal and/or alkaline earth metal is at least one member selected from the consisting of Na, K, Ca and Mg.

33. The method for decomposing an ammonium salt of a monocarboxylic acid according to any one of Items 30 to 32, wherein the monocarboxylic acid is at least one member selected from the group consisting of acetic acid, propionic acid and butyric acid.

34. The method for decomposing an ammonium salt of a monocarboxylic acid according to any one of Items 30 to 33, which includes a monocarboxylic acid recovery step in which a liquid after withdrawing the gas of a basic aqueous solution in the heating step, is heated at a temperature of at least 125° C. under reduced pressure or atmospheric pressure, to separate and recover the monocarboxylic acid.

35. The method for decomposing an ammonium salt of a monocarboxylic acid according to Item 34, wherein an ammonium salt of a monocarboxylic acid and water are mixed to the residue after separating the monocarboxylic acid in the monocarboxylic acid recovery step, and the mixture is recycled to the above heating step.

36. The method for decomposing an ammonium salt of a monocarboxylic acid according to Item 35, wherein an ammonium salt of a monocarboxylic acid and water are mixed to the above residue, and then the mixture is preheated at a temperature of at least 90° C. and then recycled to the above heating step.

EXAMPLES

Now, the present invention will be described in further detail with reference to Examples.

TABLE 1

|  | MW | m.p. | Pyne Organic Chemistry | | | Iso-electric point | Solubility at 25° C. g/ |
|  |  |  | pKa1 | pKa2 | pKa3 | pI | 100 gH$_2$O |
| --- | --- | --- | --- | --- | --- | --- | --- |
| Asparagine | 132.12 | 236 | 2.02 |  |  | 5.41 | 3.11 |
| Aspartic acid | 133.1 | 269 | 2.1 | 3.86 |  | 2.98 | 0.5 |
| Glutamic acid | 147.13 | 247 | 2.1 | 4.07 |  | 3.08 | 0.843 |
| Glutamine | 146.15 | 186 | 2.17 |  |  | 5.7 | 3.6 |
| Histidine | 155.16 | 287 | 1.77 |  |  | 7.64 | 4.29 |
| Isoleucine | 131.18 | 284 | 2.32 |  |  | 6.04 | 4.117 |
| Leucine | 131.18 | 337 | 2.33 |  |  | 6.04 | 2.19 |
| Methionine | 149.21 | 283 | 2.28 |  |  | 5.74 | 3.35 |

TABLE 1-continued

|  | Pyne Organic Chemistry | | | | Iso-electric point | Solubility at 25° C. g/ |
| --- | --- | --- | --- | --- | --- | --- |
|  | MW | m.p. | pKa1 | pKa2 | pKa3 | pI | 100 gH$_2$O |
| Phenyl-alanine | 165.19 | 283 | 2.58 | | | 5.91 | 2.965 |
| Tryptophan | 204.23 | 289 | 2.38 | | | 5.88 | 1.14 |
| Tyrosine | 181.19 | 344 | 2.2 | | | 5.66 | 0.045 |
| Valine | 117.15 | 315 | 2.29 | | | 6 | 8.85 |
| Fumaric acid | 116.07 | 299.5 | 3.03 | 4.44 | | | |
| Tartaric acid | 150.09 | 205 | 3.04 | 4.37 | | | |
| Succinic acid | 118.09 | 188 | 4.21 | 5.64 | | | |
| Maleic acid | 116.07 | 141 | 1.83 | 6.07 | | | |
| Malic acid | 134.09 | 132 | 3.40 | 5.11 | | | |
| o-Phthalic acid | 166.13 | 210 | 2.95 | 5.41 | | | |
| Glutaric acid | 147.13 | — | 4.31 | 5.41 | | | |
| Adipic acid | 146.14 | 153.4 | 4.43 | 5.41 | | | |
| Citric acid | 192.13 | 153 | 3.13 | 4.76 | 6.4 | | |
| Suberic acid | 174.2 | 142.1 | 4.52 | | | | |
| Terephthalic acid | 166.13 | | 3.51 | 4.82 | | | |

Acetic acid pKa 4.76
Propionic acid pKa 4.86
pKa of dicarboxylic acids and of propionic acid:

Handbook of Chemistry and Physics

In the following Example 1-1, diammonium succinate (manufactured by Wako Pure Chemical Industries, Ltd.) was used as a substitute material for a concentrate obtained by concentrating, in the concentration step, the ammonium salt of organic acid A obtained from a bioconversion step. Further, as acid B, acetic acid (manufactured by Wako Pure Chemical Industries, Ltd.) or propionic acid (manufactured by Wako Pure Chemical Industries, Ltd.) was used.

Example 1-1

180 g of diammonium succinate (succinic acid: 78 wt %, ammonia: 22 wt %) was dissolved in 720 g of water to prepare 900 g of a 20 wt % ammonium succinate solution.

This aqueous solution was evaporated and concentrated in an oil bath of 140° C. (the interior of the evaporator: 100° C.) to a level of 256.5 g. 249 g was taken therefrom, and 173 g of acetic acid was added to succinic acid, followed by thorough stirring. The mixture (415.5 g charge) was put into a crystallization apparatus and maintained at 100° C. for 10 minutes, and then maintained at 40° C. for 18 hours with stirring.

Then, vacuum filtration was carried out, and then the solid content was taken out. The filtrate was 296.6 g, and the solid content was 93.4 g. The obtained solid content was analyzed for organic substances by liquid chromatography and for ammonia by ion chromatography, whereby acetic acid was 28.4 wt %, succinic acid was 58.3 wt %, and ammonia was 10.4 wt %. The total was not 100%, and this is believed attributable to a measurement error, as ammonia and organic substances were analyzed separately. Likewise, the mother liquor was found to comprise 59.9 wt % of acetic acid, 25.3 wt % of succinic acid and 6.7 wt % of ammonia.

It is hardly believed that the mother liquor contained such a large amount of acetic acid, and it is believed that a substantial amount of ammonium acetate was coprecipitated. Therefore, the molar ratios (on the assumption of 100 g) were calculated and found to be as follows.

Acetic acid: 28.4/60=0.473 Carboxylic acid: 47 mol
Succinic acid: 58.3/118=0.494 Carboxylic acid: 98 mol (49×2)
Ammonia 10.4/17=0.611 Ammonia: 61 mol If it is assumed that 60% of acetic acid is in the form of ammonium acetate (28 mol), ammonia is 33 mol to 98 mol of carboxylic acid of succinic acid, whereby 16 mol (⅓ of the obtained solid) is already succinic acid itself formed by the salt decomposition, and the rest is a monoammonium salt of succinic acid. In reality, the mother liquor also contained ammonia, and it is believed that the salt decomposition proceeded more by the reactive crystallization.

Further, 90 g of the obtained solid was dissolved in 80 g of acetic acid at a temperature of about 80° C., and the solution (165 g) was put into a crystallizing apparatus and maintained at 80° C. for 10 minutes, and then maintained at 40° C. for 7 hours with stirring.

Then, vacuum filtration was carried out, and then, a solid content was taken out. The filtrate was 129.6 g, and the solid content was 16.2 g. The obtained solid content was analyzed for organic substances by liquid chromatography and for ammonia by ion chromatography, whereby acetic acid was 10.9 wt %, succinic acid was 87.4 wt % and ammonia was 2.8 wt %. Likewise, the mother liquor was found to comprise 90.2 wt % of acetic acid, 25.2 wt % of succinic acid and 6.0 wt % of ammonia.

Acetic acid: 10.9/60=0.182 Carboxylic acid: 18 mol
Succinic acid: 87.4/118=0.741 Carboxylic acid:148 mol (74×2)
Ammonia 2.8/17=0.165 Ammonia: 16 mol In this Example, it was possible to obtain succinic acid from ammonium succinate without employing electrodialysis or an inorganic acid, whereby it was confirmed that decomposition to succinic acid was carried out solely by reactive crystallization.

Example 1-2

Using a 100 ml reagent bottle, 15.2 g (0.1 mol) of diammonium succinate was mixed to 15.2 g (0.25 mol) of acetic acid and 6 g of water under heating and dissolved at 90° C. This solution was left for 12 hours in a water bath (40° C.). White solid thereby precipitated was collected by filtration. The recovered solid was 6.1 g, and as a result of the analysis, succinic acid was 69 wt %, and ammonia was 12.8 wt %.

3.1 g of this solid was again put into a 100 ml reagent bottle and mixed with 5.4 g of acetic acid under heating and dissolved at 75° C. This solution was left to stand for 8 hours in a water bath (40° C.). White solid precipitated, was collected by filtration. The recovered solid was 0.5 g, and as a result of the analysis, succinic acid was 97 wt %, and ammonia was 1.6 wt %.

Example 1-3

Using a 100 ml reagent bottle, 15 g (0.1 mol) of diammonium succinate was mixed with 35 g (0.58 mol) of acetic acid and 10 g of water under heating and dissolved at 95° C. This solution was left to stand for 12 hours in a water bath (40° C.). White solid precipitated, was collected by filtration. The recovered solid was 4.3 g.

4 g of this solid was again put into a 100 ml reagent bottle and added to 16 g of acetic acid under heating and dissolved at 70° C. This solution was left to stand at room temperature (about 15° C.) for 8 hours. White solid precipitated was collected by filtration. The recovered solid was 2.2 g, and as a result of the analysis, succinic acid was 90 wt %, and ammonia was 0.8 wt %.

From the foregoing results, it is evident that it was possible to recover succinic acid of high purity by reactive crystallization by means of acetic acid.

Example 1-4

50.35 g of diammonium succinate and 269.72 g of acetic acid were put into a crystallizing apparatus, dissolved at 85° C. and maintained for 10 minutes, and then cooled to 15° C. with stirring. Upon expiration of 22 minutes after cooling to 15° C., 1.03 g of reagent succinic acid (manufactured by Wako Pure Chemical Industries, Ltd.) was put as seed crystals, and the mixture was maintained for 4 hours.

A filtrate was 299.8 g, and a solid was recovered in an amount of 13.1 g. The obtained solid content was analyzed for organic substances by liquid chromatography and for ammonia by ion chromatography, whereby acetic acid was 19.5 wt %, succinic acid was 82.4 wt %, and ammonia was 1.1 wt %. Likewise, the mother liquor was found to comprise 80.7 wt % of acetic acid, 9.9 wt % of succinic acid and 4.0 wt % of ammonia.

Recovery rate of succinic acid: $(13.1 \times 0.824)/(50.35 \times 118/152) = 0.276$ (27.6% recovery)

Solid Molar Composition:

| | |
|---|---|
| Succinic acid | $13.1 \times 0.824/118 = 0.0915$ |
| Acetic acid | $13.1 \times 0.195/60 = 0.0425$ |
| Ammonia | $13.1 \times 0.011/17 = 0.0084$ |

Example 1-5

50.46 g of diammonium adipate (manufactured by Wako Pure Chemical Industries, Ltd.) and 269.83 g of acetic acid were put into a crystallizing apparatus, dissolved at 85° C. and maintained for 10 minutes, and then cooled to 15° C. with stirring. Precipitation started immediately, and the system was left to stand for 4 hours and 23 minutes.

A filtrate was 253.4 g, and a solid was recovered in an amount of 55.4 g. The obtained solid content was analyzed for organic substances by liquid chromatography and for ammonia by ion chromatography, whereby acetic acid was 47.1 wt %, adipic acid was 61.8 wt % and ammonia was 2.0 wt %. Likewise, the mother liquor was found to comprise 85.0 wt % of acetic acid, 5.1 wt % of adipic acid and 3.7 wt % of ammonia.

Recovery rate of adipic acid: $(55.4 \times 0.618)/(50.46 \times 150.1/184.2) = 0.832$ (83.2% recovery)

Solid Molar Composition:

| | |
|---|---|
| Adipic acid | $55.4 \times 0.618/150.1 = 0.228$ |
| Acetic acid | $55.4 \times 0.471/60 = 0.434$ |
| Ammonia | $55.4 \times 0.02/17 = 0.065$ |

50.21 g of the obtained solid content was washed at 16° C. for 30 minutes by using 149.78 g of acetic acid, followed by filtration. The obtained solid was 25.9 g, and the rinsing liquid was 169.5 g. The solid was analyzed, whereby acetic acid was 11.6 wt %, adipic acid was 80.3 wt % and ammonia was 0.2 wt %. Likewise, the rinsing liquid was found to comprise 89.4 wt % of acetic acid, 3.9 wt % of adipic acid and 0.5 wt % of ammonia.

Recovery rate of adipic acid: $(25.9 \times 0.803)/(50.46 \times 150.1/184.2) = 0.505$ (50.5% recovery)

Solid Molar Composition:

| | |
|---|---|
| Adipic acid | $25.9 \times 0.803/150.1 = 0.139$ |
| Acetic acid | $25.9 \times 0.116/60 = 0.050$ |
| Ammonia | $25.9 \times 0.002/17 = 0.003$ |

Example 1-6

6.08 g of monoammonium glutamate (manufactured by Sigma Co.) was dissolved in 10.08 g of water. 399.69 g of acetic acid was put into a crystallizing apparatus and maintained at 60° C., and 15.72 g of the aqueous monoammonium glutamate solution was introduced thereinto. Turbidity started immediately, and the system was cooled to 16° C. with stirring. The system was left to stand at 16° C. for 4 hours and 18 minutes.

A filtrate was 387.1 g, and a solid was recovered in an amount of 19.3 g. The obtained solid content was analyzed for organic substances by liquid chromatography and for ammonia by ion chromatography, whereby acetic acid was 68.2 wt %, glutamic acid was 24.7 wt % and ammonia was 0.15 wt %. Likewise, the mother liquor was found to comprise 92.3 wt % of acetic acid, no glutamic acid detected and 1.4 wt % of ammonia. The rest of the mother liquor is assumed to be water.

Recovery rate of glutamic acid: $(19.3 \times 0.247)/(6.08 \times 197.1/214.2 \times 15.72/16.16) = 0.876$ (87.6% recovery)

Solid Molar Composition:

| | |
|---|---|
| Glutamic acid | $19.3 \times 0.247/197.1 = 0.0247$ |
| Acetic acid | $19.3 \times 0.682/60 = 0.224$ |
| Ammonia | $19.3 \times 0.0015/17 = 0.0017$ |

Example 1-7

Using a 100 ml reagent bottle, 50.42 g of 28% aqueous ammonia (manufactured by Kanto Kagaku K. K.) (0.83 mol of ammonia) was added to 15 g (0.086 mol) of suberic acid (manufactured by Acros Organics Co.) for dissolution. This solution was dried at 80° C. under reduced pressure to obtain a salt. Upon the analysis, suberic acid was 77 wt %, and ammonia was 9.2 wt %, and it was found that 62% of the carboxyl group of suberic acid became an ammonium salt.

5.01 g of this ammonium salt of suberic acid was dissolved in 25.05 g of acetic acid under heating, and this solution was left to stand in a constant temperature vessel at 15° C. for 18 hours. White solid precipitated, was collected by filtration. The recovered solid was 0.46 g, and as a result of the analysis, suberic acid was 55 wt %, acetic acid was 40 wt % and ammonia was 0.2 wt %. The mother liquor was 29.60 g, and as a result of the analysis, suberic acid was 2.6 wt %, acetic acid was 93 wt % and ammonia was 1.3 wt %.

Recovery rate of suberic acid: $(0.46 \times 0.55)/(5.01 \times 0.62) = 0.081$ (8.1% recovery)

Solid Molar Composition:

| | |
|---|---|
| Suberic acid | 0.46 × 0.55/174 = 0.00145 |
| Acetic acid | 0.46 × 0.40/60 = 0.00307 |
| Ammonia | 0.46 × 0.002/17 = 0.00005 |

Example 1-8

50.20 g of diammonium adipate (manufactured by Wako Pure Chemical Industries, Ltd.) and 399.29 g of acetic acid were put into a crystallizing apparatus, dissolved at 95° C. and maintained for 10 minutes, and then cooled to 15° C. with stirring. Upon expiration of 55 minutes after the temperature became 15° C., 0.5 g of adipic acid (manufactured by Wako Pure Chemical Industries, Ltd.) was added as seed crystals. The system was left to stand for 3 hours and then subjected to filtration.

The mother liquor (the filtrate) was 420.5 g, and a solid was recovered in an amount of 25.65 g. The obtained solid content was analyzed for organic substances by liquid chromatography and for ammonia by ion chromatography, whereby propionic acid was 35.3 wt %, adipic acid was 56.8 wt %, and ammonia was 5.5 wt %. Likewise, the mother liquor was found to comprise 90.6 wt % of propionic acid, 6.2 wt % of adipic acid and 2.2 wt % of ammonia.

Recovery rate of adipic acid: (25.65×0.568)/(50.20×150.1/184.2)=0.356 (35.6% recovery)

Solid Molar Composition:

| | |
|---|---|
| Adipic acid | 25.65 × 0.568/150.1 = 0.097 |
| Propionic acid | 25.65 × 0.353/74 = 0.127 |
| Ammonia | 25.65 × 0.055/17 = 0.086 |

25.2 g of the obtained solid content was dissolved at 95° C. by using 99.99 g of propionic acid and then cooled to 15° C. Precipitation started immediately. The system was left to stand for 3 hours and 53 minutes and then subjected to filtration. The obtained solid was 16.48 g, and the mother liquor was 104.4 g. The solid was analyzed, whereby propionic acid was 28.2 wt %, adipic acid was 69.0 wt % and ammonia was 0.4 wt %. Likewise, the mother liquor was found to comprise 94.4 wt % of propionic acid, 3.3 wt % of adipic acid and 1.1 wt % of ammonia.

Recovery rate of adipic acid: (16.48×0.568)/(25.2×0.690)=0.794 (79.4% recovery)

Solid Molar Composition:

| | |
|---|---|
| Adipic acid | 16.48 × 0.690/150.1 = 0.076 |
| Propionic acid | 16.48 × 0.282/74 = 0.063 |
| Ammonia | 16.48 × 0.004/17 = 0.004 |

Example 2

Now, a test for distillation of a monocarboxylic acid and an ammonium salt of the monocarboxylic acid, will be described.

Preparation of Model Mother Liquors

① Preparation of Model Mother Liquor 1

The composition of the mother liquor after reactive crystallization will be influenced by the amount of the solvent in the reactive crystallization and the purity of the solvent at the time of recycling and will be determined by the optimum operational condition by such a condition as utility. To see the difference in separation performance based on the melting point of the ammonium salt of a monocarboxylic acid, as the monocarboxylic acid, acetic acid was selected, which is considered to be preferred among those having from 1 to 6 carbon atoms, as disclosed in JP-A-2002-135656. The type of the di/tricarboxylic acid gives no influence on the separation of the monocarboxylic acid and the ammonium salt of the monocarboxylic acid, although its influence over the boiling point slightly differs. In the present Test Examples, as the di/tricarboxylic acid, succinic acid was selected as a standard substance.

The solubility of ammonium succinate in acetic acid was confirmed to be such that it dissolved up to a concentration of 33 wt % at 100° C. and up to 10 wt % at 16° C. Therefore, on the assumption that the temperature of industrial water is about 20° C., the crystallization temperature was assumed to be from about 30 to 50° C., and it was assumed that it would remain at a concentration of about 20 wt % in the crystallization mother liquor after the crystallizing operation. Therefore, assuming a crystallization mother liquor obtained by separating succinic acid precipitated by reactive crystallization by means of acetic acid, about 120 g of acetic acid manufactured by Wako Pure Chemical Industries, Ltd. and about 30 g of ammonium succinate manufactured by Wako Pure Chemical Industries, Ltd. were mixed, heated and completely dissolved to obtain a solution having an ammonium succinate concentration of about 20 wt %, which was designated as "model mother liquor 1". As mentioned above:

| | | |
|---|---|---|
| Succinic acid primary pKa: | | 4.21 |
| Succinic acid secondary pKa: | | 5.64 |
| Acetic acid pKa: | | 4.76. |

Accordingly, it is considered that while this model mother liquor 1 comprises:

| | | |
|---|---|---|
| Charge: | Acetic acid | 120 g (2 mol) |
| | Diammonium succinate | 30.4 g (0.2 mol, about 20 wt %), the diammonium succinate is reacted with acetic acid to have approximately the following composition: |
| Dissolved liquid: | Acetic acid | 108 g (1.8 mol) |
| | Monoammonium succinate | 27 g (0.2 mol) |
| | Ammonium acetate | 15.4 g (0.2 mol) |

② Preparation of Model Mother Liquor 2

Propionic acid manufactured by Wako Pure Chemical Industries, Ltd., diammonium succinate manufactured by Wako Pure Chemical Industries, Ltd. and 28% aqueous. ammonia manufactured by Wako Pure Chemical Industries, Ltd. were mixed in the following ratio, heated and completely dissolved to obtain a solution, which was designated as "model mother liquor 2".

| | | |
|---|---|---|
| Charge: | Propionic acid | 98.75 g (1.33 mol) |
| | Diammonium succinate | 20.29 g (0.133 mol) |
| | 28% aqueous ammonia | 13.32 g (0.22 mol: ammonia) |

-continued

This model mother liquor 2 comprises:

| | |
|---|---|
| Succinic acid primary pKa: | 4.21 |
| Succinic acid secondary pKa: | 5.64 |
| Propionic acid pKa: | 4.67. |

Accordingly, it is considered that the diammonium succinate is reacted with propionic acid to have approximately the following composition

| Dissolved liquid: | Propionic acid | 1.2 mol (88.8 g) |
|---|---|---|
| | Monoammonium succinate | 0.133 mol |
| | Ammonium propionate | 0.35 mol |
| | | (0.22 mol + 0.133 mol) |
| | Water | 9.6 g (7.2 wt %) |

Distillation Tests

Test Example 2-1

The Lower Limit Temperature

Model mother liquor 1 (acetic acid: 120.00 g, diammonium succinate: 30.42 g) was prepared, and then this mother liquor was put into a 200 ml eggplant type flask, installed in a simple distillation apparatus and subjected to simple distillation at 10 mmHg. A condenser of water-cooling type was employed. A very small amount of nitrogen gas was constantly circulated in the simple distillation apparatus for the purpose of preventing bumping and for the purpose of increasing the distillation efficiency.

When the temperature in the flask became 36° C., distillation started, and when it became 69° C., no substantial distillate was observed, and the distillation was terminated. In the flask, precipitation occurred and solidification was observed.

The distilled amount was 40 ml (45.65 g). The amount of the content in the flask was 64.78 g from deduction of the tare of the flask and the balance between before and after the test. It is believed that the rest was not sufficiently condensed in the condenser and was released from the reduced pressure line to a draft, since the temperature of the cooling water of the condenser was high as compared with the degree of reduced pressure.

Text Example 2-2

Upper Limit Temperature

Model mother liquor 1 (acetic acid: 120.18 g, diammonium succinate: 30.40 g) was prepared, then put into a 200 ml eggplant type flask, installed in a simple distillation apparatus and subjected to simple distillation at 150 mmHg. A condenser of water cooling type was used. A very small amount of nitrogen gas was constantly circulated to the simple distillation apparatus for the purpose of preventing bumping and for the purpose of increasing the distillation efficiency.

When the temperature in the flask became 85° C., distillation started, and after the temperature of an oil bath became 105° C., distillation was continued while reducing the pressure by 10 mmHg each time. Upon expiration of 1 hour and 45 minutes, the distilled amount reached 40 ml. Here, the first distillate sample was recovered. At that time, the temperature in the flask was 89° C., and the pressure was 120 mmHg.

Thereafter, an operation of reducing the pressure when the distillation stopped, was repeated, so that the temperature of the flask would not exceed 100° C. The temperature of the oil bath was controlled not to exceed the melting point (114° C.) taking into consideration a fluctuation or error of the thermometer, and 109° C. was the maximum. Upon expiration of 1 hour and 47 minutes from the first sampling, a sample was collected when 40 ml was distilled. At that time, the temperature in the flask was 95° C., and the pressure was 60 mmHg.

The pressure was returned to atmospheric pressure, 2.55 g of the bottom sample was collected. The amount of the content in the flask was 64.96 g from deduction of the tare of the flask and the balance between before and after the test. No precipitation of crystals was observed throughout the period of the simple distillation.

Text Example 2-3

Excess Temperature

Model mother liquor 1 (acetic acid: 120.03 g, diammonium succinate: 30.41 g) was prepared, then put into a 200 ml eggplant type flask, installed in a simple distillation apparatus and subjected to simple distillation at 380 mmHg. A condenser of water cooling type was used. A very small amount of nitrogen gas was constantly circulated to the simple distillation apparatus for the purpose of preventing bumping and for the purpose of increasing the distillation efficiency.

When the temperature in the flask became 110° C., distillation started, and in about 1 hour, the temperature reached 114° C. Thereafter, the distillation rate did not increase, and in further 45 minutes, the distilled amount reached 40 ml (corresponding to Test Example 2-1). Here, the first distillate sample was recovered. At that time, the temperature was 118° C. When further 40 ml was distilled, (132° C.; upon expiration of 1 hour and 10 minutes from the first sampling), the pressure was once returned to atmospheric pressure, and the second distillate sample and 2.55 g of the bottom sample were collected. The pressure was again reduced to 380 mmHg, and when 2.97 g was distilled, the distillation was terminated. The amount of the content in the flask was 54.47 g from deduction of the tare of the flask and the balance between before and after the test. No precipitation of crystals was observed throughout the period of the simple distillation.

Text Example 2-4

Effect of Water

In the same manner as for model mother liquor 1, 30.40 g of succinic acid was used. Instead of 120 g of acetic acid in model mother liquor 1, 72.02 g of acetic acid and 48.01 g of water were used to dissolve the succinic acid.

The solution was put into a 200 ml eggplant type flask, installed in a simple distillation apparatus and subjected to simple distillation at atmospheric pressure. A condenser of water cooling type was used. A very small amount of nitrogen gas was constantly circulated to the simple distillation apparatus for the purpose of preventing bumping and for the purpose of increasing the distillation efficiency.

When the temperature in the flask became 132° C. (oil bath temperature: 158° C.), distillation started, and in 20 minutes, 40 ml (42.64 g) was distilled, and a sample was collected. Further, over a period of 34 minutes, 40 ml (41.88 g) was distilled (the temperature in the flask: 150° C., oil bath: 180° C.), and a sample was collected. At that time, from the bottom, 2.71 g was sampled. Further, heating was continued, and when 20 ml (22.08 g) was distilled (the temperature in the flask: 169° C., oil bath: 206° C.), the distillation was terminated, and the distillate and the bottom were, respectively, sampled. The bottom was 39.27 g from deduction of the tare of the flask and the balance between before and after the test.

Text Example 2-5

In the Case of Propionic Acid

Model mother liquor 2 was put into a 200 ml eggplant type flask and installed in a simple distillation apparatus. After reducing the pressure to 100 mmHg, heating was initiated. A condenser of water cooling type was used. A very small amount of nitrogen gas was constantly circulated to the simple distillation apparatus for the purpose of preventing bumping and for the purpose of increasing the distillation efficiency.

When the temperature in the flask became 72° C., distillation started. When the temperature in the flask became 83° C., the pressure was reduced to maintain the temperature, and thus the pressure was reduced to 50 mmHg. Subsequently, when the temperature became 90° C. and upon expiration of 55 minutes from the initiation of the distillation, the distillate was sampled. At the at that time, the temperature of the oil bath was 100° C. Upon expiration of 1 hour from the initiation of the distillation, distillation was continued for 20 minutes by raising the temperature to 105° C. and further for 20 minutes by raising the temperature to 108° C., whereupon the bottom and the distillate were sampled. The temperature in the flask upon completion of the distillation was 95° C.

The first distillate recovered was 37.0 g, the second distillate was 15.25 g, and the bottom was 79.7 g.

In Test Example 2-5, on the same basis as for the analysis, i.e. on the assumption that the acid and the base are separately present, the charge comprised:

| | |
|---|---|
| Propionic acid | 98.75 g |
| Ammonia | 20.29 × 34/152 + 13.32 × 0.28 = 8.27 g |
| Succinic acid | 20.29 × 118/152 + 15.75 g |
| Water | 13.32 × 0.72 = 9.59 g. |

Text Example 2-6

The Minimum Temperature for Vaporization of Ammonium Acetate

Taking into consideration, the results of Test Examples 2-1 and 2-2, vaporization of ammonium acetate in an acetic acid-succinic acid system was investigated by means of the following model solution.

29.99 g of acetic acid, 15.19 g of ammonium succinate and further 7.69 g of ammonium acetate in order to more accurately grasp the vaporization of ammonium acetate, were put into a 200 ml eggplant type flask and installed in a rotary evaporator. The pressure was reduced to 30 mmHg, and the flask was immersed in an oil bath heated to 108° C. and heated for 27 minutes.

At a condenser portion, white solid was precipitated and deposited. The bottom was white solid which was precipitated and solidified, and its amount was 27.93 g.

On the same basis as for the analysis, i.e. on the assumption that the acid and the base are present separately, the charge comprised:

| | |
|---|---|
| Acetic acid | 29.99 + 7.69 × 60/77 = 35.98 g |
| Ammonia | 15.19 × 34/152 + 7.69 × 17/77 = 5.10 g |
| Succinic acid | 15.19 × 118/152 = 11.79 g. |

Text Example 2-7

Maximum Temperature for Vaporization of Ammonium Acetate

On the basis of the results of Test Examples 2-1 and 2-2 and further in consideration of an idea that it may be advantageous to add water under a high temperature condition in view of Test Examples 2-3 and 2-4, vaporization of ammonium acetate in an acetic acid-succinic acid system was investigated by means of the following model solution.

24.00 g of acetic acid, 15.20 g of ammonium succinate, 6.11 g of deionized water and further 7.68 g of ammonium acetate in order to more accurately grasp the vaporization of ammonium acetate, were put into a 200 ml eggplant type flask and installed in a rotary evaporator. The pressure was reduced to 150 mmHg, and the flask was immersed in an oil bath heated to 150° C., whereupon the oil bath was heated to 178° C. The distillation rate became slow immediately, but in consideration of comparison to Test Example 2-6, heating was continued for 30 minutes.

At a condenser portion, white solid was precipitated and deposited. The bottom was white solid which was precipitated and solidified, and its amount was 16.07 g.

On the same basis as for the analysis, i.e. on the assumption that the acid and the base are present separately, the charge comprised:

| | |
|---|---|
| Acetic acid | 24.00 + 7.68 × 60/77 = 35.98 g |
| Ammonia | 15.20 × 34/152 + 7.68 × 17/77 = 5.10 g |
| Succinic acid | 15.20 × 118/152 = 11.80 g. |

Text Example 2-8

30.00 g of acetic acid, 15.18 g of ammonium succinate and further, 7.71 g of ammonium acetate in order to more accurately grasp the vaporization of ammonium acetate, were put into a 200 ml eggplant type flask and installed in a rotary evaporator. The pressure was reduced to 50 mmHg, and the flask was immersed in an oil bath heated to 100° C. When the temperature of the oil bath became 132° C., distillation started, and 25 minutes later, the bottom underwent precipitation and solidification at 139° C., and the distillation was terminated. The amount of the bottom was 22.71 g. At a condenser portion, white solid was precipitated and deposited.

On the same basis as for the analysis, i.e. on the assumption that the acid and the base are separately present, the charge comprised:

| | |
|---|---|
| Acetic acid | 30.00 + 7.71 × 60/77 = 36.01 g |
| Ammonia | 15.18 × 34/152 + 7.71 × 17/77 = 5.10 g |
| Succinic acid | 15.18 × 118/152 = 11.78 g. |

Text Example 2-9

Effects of Water

On the basis of the results of Test Examples 2-1 and 2-2 and in consideration of an idea that it may be advantageous to add water in view of Test Example 2-3 and 2-4, the vaporization of ammonium acetate in an acetic acid-succinic acid system was investigated by means of the following model solution on the assumption that water is added or to be added to the crystallization solvent. 7.50 g of acetic acid, 15.23 g of ammonium succinate, 35.99 g of deionized water and further, 7.68 g of ammonium acetate in order to more accurately grasp the vaporization of ammonium acetate, were put into a 200 ml eggplant type flask and installed in a rotary evaporator. The pressure was reduced to 50 mmHg, and the flask was immersed in an oil bath heated to 137° C. During the test, the temperature of the oil bath changed within a range of from 137 to 138° C.

The distillation was complete in 17 minutes, and the bottom was white solid which was precipitated and solidified, and its amount was 27.96 g. At a condenser portion, white solid was precipitated and deposited.

On the same basis as for the analysis, i.e. on the assumption that the acid and the base are separately present, the charge comprised:

| | |
|---|---|
| Acetic acid | 7.50 + 7.68 × 60/77 = 13.48 g |
| Ammonia | 15.23 × 34/152 + 7.68 × 17/77 = 5.10 g |
| Succinic acid | 15.23 × 118/152 = 11.82 g. |

Text Example 2-10

Vaporization of Ammonium Propionate

Ammonium propionate is not commercially available. Therefore, 39.99 g of propionic acid, 15.23 g of ammonium succinate and 15.16 g of 28% aqueous ammonia manufactured by Wako Pure Chemical Industries, Ltd. were used as a model solution.

This model solution was put into an eggplant type flask and installed in a rotary evaporator. The pressure was reduced to 40 mmHg, and the flask was immersed in an oil bath heated to 157° C. The temperature was 160° C. during the test. In this state, distillation was carried out for 25 minutes.

At a condenser portion, white solid was precipitated and deposited. The bottom was white solid which was precipitated and solidified, and its amount was 25.38 g.

On the same basis as for the analysis, i.e. on the assumption that acid and base are separately present, the charge comprised:

| | |
|---|---|
| Propionic acid | 39.99 g |
| Ammonia | 15.20 × 34/152 + 15.16 × 0.28 = 3.41 g |
| Succinic acid | 15.23 × 118/152 = 11.82 g. |

Results

The results of the foregoing distillation tests are shown in Tables 2-1 to 2-4.

TABLE 2-1

Simple distillation: Corresponding to a kettle type evaporator

| | | Pressure (mmHg) | Maximum temp. in the oil bath (° C.) | Maximum liquid temp. in the flask (° C.) | Overall time | Charged acetic acid (g) | Charged ammonia (g) | Charged succinic acid (g) | Charged water (g) |
|---|---|---|---|---|---|---|---|---|---|
| Ex. 1 | Distillate | 10 | 77 | 69 | 2 hr | | | | |
| | Bottom | 10 | 77 | 69 | 2 hr | | | | |
| | Balance | | | | | 120.00 | 6.80 | 23.62 | 0.00 |
| Ex. 2 | Distillate 1 | 150–60 | 105 | 89 | 1 hr 45 min | | | | |
| | Distillate 2 | 150–60 | 109 | 95 | 3 hr 19 min | | | | |
| | Bottom | 150–60 | 109 | 95 | 3 hr 19 min | | | | |
| | Balance | | | | | 120.18 | 6.80 | 23.60 | 0.00 |
| Ex. 3 | Distillate 1 | 380 | 134 | 118 | 1 hr 40 min | | | | |
| | Distillate 2 | 380 | 149 | 132 | 3 hr 47 min | | | | |
| | Bottom 1 | 380 | 149 | 132 | 3 hr 47 min | | | | |
| | Bottom 2 | 380 | 160 | 132 | 4 hr 25 min | | | | |
| | Balance (bottom 1) | | | | | 120.03 | 6.80 | 23.61 | 0.00 |
| Ex. 4 | Distillate 1 | 760 | 142 | 116 | 53 min | | | | |
| | Distillate 2 | 760 | 160 | 139 | 2 hr 36 min | | | | |
| | Distillate 3 | 760 | 175 | 156 | 3 hr 48 min | | | | |
| | Bottom 1 | 760 | 160 | 139 | 2 hr 36 min | | | | |
| | Bottom 2 | 760 | 175 | 156 | 3 hr 48 min | | | | |
| | Balance (bottom 1) | | | | | 72.02 | 6.80 | 23.60 | 48.01 |
| Ex. 5 | Distillate 1 | 100–50 | 97–100 | 72–90 | 55 min | * | | | |
| | Distillate 2 | 100–50 | 100–108 | 90–95 | 1 hr 40 min | | | | |

TABLE 2-1-continued

Simple distillation: Corresponding to a kettle type evaporator

|  | Pressure (mmHg) | Maximum temp. in the oil bath (° C.) | Maximum liquid temp. in the flask (° C.) | Overall time | Charged acetic acid (g) | Charged ammonia (g) | Charged succinic acid (g) | Charged water (g) |
|---|---|---|---|---|---|---|---|---|
| Bottom | 100–50 | 97–108 | 72–95 | 1 hr 40 min | | | | |
| Balance | | | | | 98.75 | 8.27 | 15.75 | 9.59 |

* Propionic acid

TABLE 2-2

Simple distillation: Corresponding to a kettle type evaporator

|  |  | Acetic acid (g) | Ammonia (g) | Succinic acid (g) | Total Amide (g) | Amidated ammonia | Distilled ammonia | Ammonia in bottle 1 | |
|---|---|---|---|---|---|---|---|---|---|
| Ex. 1 | Distillate | 46.69 | 0.03 | 0.00 | 0.00 | | | | |
| | Bottom | 33.87 | 6.71 | 23.14 | 0.00 | 0.00 | 0.00 | 0.39 | mol |
| | Balance | 80.56** | 6.73 | 23.14 | 0.00 | 0.00 | 0.00 | 1.00 | mol fraction |
| Ex. 2 | Distillate 1 | 42.14 | 0.15 | 0.00 | 0.00 | | | | |
| | Distillate 2 | 42.76 | 0.05 | 0.00 | 0.00 | | | | |
| | Bottom | 34.97 | 6.35 | 21.99 | 1.21 | 0.01 | 0.01 | 0.37 | mol |
| | Balance | 119.88 | 6.54 | 21.99 | 1.21 | 0.03 | 0.03 | 0.94 | mol fraction |
| Ex. 3 | Distillate 1 | 41.72 | 0.05 | 0.00 | 0.00 | | | | |
| | Distillate 2 | 40.36 | 0.01 | 0.00 | 0.00 | | | | |
| | Bottom 1 | 29.58 | 3.67 | 10.81 | 11.88 | 0.11 | 0.00 | 0.22 | mol |
| | Bottom 2 | 25.32 | 2.99 | 8.57 | 13.07 | 0.32 | 0.01 | 0.66 | mol fraction |
| | Balance (bottom 1) | 111.66 | 3.74 | 10.81 | 11.88 | | | | |
| Ex. 4 | Distillate 1 | 16.48 | 0.01 | 0.00 | 0.00 | | | | |
| | Distillate 2 | 21.47 | 0.02 | 0.00 | 0.00 | | | | |
| | Distillate 3 | 11.28 | 0.05 | 0.00 | 0.00 | | | | |
| | Bottom 1 | 31.90 | 4.52 | 14.67 | 9.30 | 0.08 | 0.00 | 0.27 | mol |
| | Bottom 2 | 14.66 | 1.66 | 5.69 | 15.58 | 0.23 | 0.01 | 0.75 | mol fraction |
| | Balance (bottom 1) | 69.86 | 4.56 | 14.67 | 9.30 | | | | |
| Ex. 5 | Distillate 1 | *26.20 | 0.28 | 0.00 | 0.00 | | | | |
| | Distillate 2 | 13.70 | 0.56 | 0.00 | 0.00 | | | | |
| | Bottom | 54.29 | 7.34 | 14.50 | 0.20 | 0.00 | 0.05 | 0.43 | mol |
| | Balance | 94.19 | 8.18 | 14.50 | 0.20 | 0.00 | 0.10 | 0.89 | mol fraction |

*Propionic acid
**(Partly leaked without being condensed)

TABLE 2-3

Rotary evaporator: Corresponding to a thin film type evaporator

|  |  | Pressure (mmHg) | Maximum temp. in the oil bath (° C.) | Maximum liquid temp. in the flask (° C.) | Overall time | Charged acetic acid (g) | Charged ammonia (g) | Charged succinic acid (g) | Charged water (g) |
|---|---|---|---|---|---|---|---|---|---|
| Ex. 6 | Distillate | 30 | 108–110 | UM | 27 min | | | | |
| | Bottom | 30 | 108–110 | UM | 27 min | | | | |
| | Balance | | | | | 35.98 | 5.10 | 11.79 | 0.00 |
| Ex. 7 | Distillate | 150 | 150–178 | UM | 30 min | | | | |
| | Bottom | 150 | 150–178 | UM | 30 min | | | | |
| | Balance | | | | | 29.98 | 5.10 | 11.80 | 6.11 |
| Ex. 8 | Distillate | 50 | 132–139 | UM | 25 min | | | | |
| | Bottom | 50 | 132–139 | UM | 25 min | | | | |
| | Balance | | | | | 36.01 | 5.10 | 11.78 | 0.00 |

TABLE 2-3-continued

Rotary evaporator: Corresponding to a thin film type evaporator

| | | Pressure (mmHg) | Maximum temp. in the oil bath (° C.) | Maximum liquid temp. in the flask (° C.) | Overall time | Charged acetic acid (g) | Charged ammonia (g) | Charged succinic acid (g) | Charged water (g) |
|---|---|---|---|---|---|---|---|---|---|
| Ex. 9 | Distillate | 50 | 137–138 | UM | 17 min | | | | |
| | Bottom | 50 | 137–138 | UM | 17 min | | | | |
| | Balance | | | | | 13.48 | 5.10 | 11.82 | 35.99 |
| Ex. 10 | Distillate | 40 | 157–160 | UM | 25 min | * | | | |
| | Bottom | 40 | 157–160 | UM | 25 min | | | | |
| | Balance | | | | | 39.99 | 3.41 | 11.82 | 0.00 |

UM: Unmeasurable
* Propionic acid

TABLE 2-4

Rotary evaporator: Corresponding to a thin film type evaporator

| | | Acetic acid (g) | Ammonia (g) | Succinic acid (g) | Total Amide (g) | Amidated ammonia | Distilled ammonia | Ammonia in bottle | |
|---|---|---|---|---|---|---|---|---|---|
| Ex. 6 | Distillate | 4.32 | 0.08 | 0.00 | 0.00 | (Calculated value) | | | |
| | Bottom | 12.68 | 3.50 | 11.69 | 0.07 | 0.0006 | 0.09 | 0.21 | mol |
| | Balance | 17.00*** | 3.59 | 11.69 | 0.07 | 0.00 | 0.31 | 0.69 | mol fraction |
| Ex. 7 | Distillate | 15.05 | 1.45 | 0.00 | 0.00 | (Calculated value) | | | |
| | Bottom | 2.37 | 1.52 | 9.56 | 2.28 | 0.0197 | 0.19 | 0.09 | mol |
| | Balance | 17.43*** | 2.98 | 9.56 | 2.28 | 0.07 | 0.64 | 0.30 | mol fraction |
| Ex. 8 | Distillate | 5.64 | 0.14 | 0.00 | 0.00 | (Calculated value) | | | |
| | Bottom | 7.60 | 2.88 | 12.25 | 0.16 | 0.0014 | 0.13 | 0.17 | mol |
| | Balance | 14.44*** | 3.02 | 12.25 | 0.16 | 0.00 | 0.43 | 0.57 | mol fraction |
| Ex. 9 | Distillate | 0.51 | 0.04 | 0.00 | 0.00 | (Calculated value) | | | |
| | Bottom | 10.39 | 4.28 | 11.79 | 0.00 | 0.0000 | 0.05 | 0.25 | mol |
| | Balance | 10.90*** | 4.32 | 11.79 | 0.00 | 0.00 | 0.16 | 0.84 | mol fraction |
| EX. 10 | Distillate | *13.60 | 2.54 | 0.00 | 0.00 | (Calculated value) | | | |
| | Bottom | 2.77 | 1.30 | 10.45 | 1.20 | 0.0103 | 0.11 | 0.08 | mol |
| | Balance | 16.37*** | 3.84 | 10.45 | 1.20 | 0.05 | 0.57 | 0.38 | mol fraction |

*Propionic acid
***(Solid precipitated in the condenser)

Discussion

In a succinic acid-acetic acid system, an ammonium salt of acid B is meant for ammonium acetate, and its melting point is known to be 114° C. In Test Example 2-3, the oil bath was from 134° C. to 149° C., and the liquid temperature in the flask exceeded 114° C., and the maximum was 132° C. The elapsed time was about 2 hours. At that time, acetamide was formed as much as 7.4 wt %, and further, succinic acid amide, etc. were formed. Succinic acid introduced, was 30.4 g (corresponding to 0.2 mol) as ammonium succinate, and succinic acid remaining in the bottom decreased to a level of 0.09 mol. Whereas, in Test Example 2-2, the temperature of the oil bath i.e. the wall temperature of the flask was 109° C., the liquid temperature in the flask was 95° C., and the elapsed time was as much as 3.3 hours. Nevertheless, acetamide was formed only at a level of 0.4 wt %, and likewise, succinic acid was 30.4 g (corresponding to 0.2 mol) as ammonium succinate, and it corresponds to 0.186 mol in such a state that it is not detected in the distillate. Thus, the difference is distinct.

From such results, the present inventor considered that there must be a temperature which is specifically influential over the reaction for amidation of ammonium carboxylate at a level of around 120° C. as an average temperature during the operation, which is higher than the liquid temperature of 95° C. in Test Example 2-2 and which is not higher than the liquid temperature of 132° C. in Test Example 2-3.

The melting point of ammonium acetate is 114° C., and as mentioned above, the melting point of ammonium propionate is considered to be about 100° C.

In these tests, the operation temperature is assumed to be about the melting point or slightly higher than the melting point. Accordingly, especially in the distillate 2, it is considered that ammonia is slightly evaporated by pyrolysis. However, during the majority of the elapsed time, the temperature in the flask is not higher than 95° C., amidation is observed to be not extremely advanced. In the case of acetic acid in Test Example 2-2, the retention time exceeded 3 hours, and the temperature was at least 90° C. for about 1 hour and a half. In the case of Test Example 2-5, taking into consideration the retention of about 40 minutes, the amidation ratio may be regarded as substantially the same within a range of analytical error.

It is important that acetic acid or propionic acid as acid B is taken out in a state where it contains no ammonia, and organic acid A and its ammonium salt are concentrated while avoiding amidation or imidation. For such a purpose, it is necessary to take as a threshold whichever is lower, about 110° C. as the reaction singular point or the melting point of acid B. Accordingly, in the case of acetic acid, the reaction singular point is unclear in a strict sense and substantially the same temperature as the melting point, and accordingly, an operational condition is adjusted at a temperature not higher than 114° C. as the melting point of acetic acid. In the case of propionic acid, the melting point of propionic acid is unclear, and in the Test Example, the evaporated amount of ammonia is not higher than 1/10 of the charged amount in spite of such a long retention time as 1 hour and 40 minutes, and such is considered to be practically within an allowable range, and therefore, a temperature of the level in this Test Example is considered to be the upper limit temperature. Namely, it is 110° C. in consideration of the temperature of the wall surface (the temperature of the oil bath). The temperature of the wall surface is not usually measured, and therefore, 110° C. as the temperature of the utility to be used for heating will be the upper limit. This corresponds to a liquid temperature of 100° C., which may be considered as corresponding to the melting point of ammonium propionate. Accordingly, in the case where propionic acid is employed, the temperature of the process fluid being at most 100° C. will be the operational condition. It is only required that the operational condition of either the utility or the process fluid is satisfied.

Further, as Comparative Examples, Test Examples 2-3 and 2-4 were carried out. This is based on an idea that the amidation or imidation reaction may be suppressed when water is contained. Under the conditions of Test Examples 2-1 and 2-2, amidation or imidation is slight, and no significant difference can be observed within a range of analytical error. Accordingly, the investigation is made intentionally under a condition where amidation or imidation takes place. From the results, a significant difference is distinctly observed. Thus, it can be said that it is advisable that water is present to some extent during the vaporization of acid B.

In a test on a method of vaporizing an ammonium salt of acid B after vaporization of acid B from the crystallization mother liquor, not negligible is the retention time. As mentioned above, the reaction for amidation becomes rapid at a temperature of about 120° C. On the other hand, a higher temperature is required to separate the ammonium salt of acid B from organic acid A and its ammonium salt, since a temperature of at least the melting point of the ammonium salt of acid B is ideal.

In the case of a simple distillation apparatus, a connecting portion from the flask as the heating portion to a condenser portion, is exposed to the outside air, whereby the outside air and the process undergo heat exchange to cause an internal reflux. Consequently, unless the difference between the heat release at the connecting portion and the heating at the flask portion is substantially large, the retention time increases. In Test Example 2-3, the temperature of the oil bath was rapidly raised, and the heating calorie was large. Nevertheless, the retention time was long, because the temperature difference between the process and the outside air became also large, and the heat release at the connecting portion became likewise large.

Therefore, the present inventor conducted a test in which a rotary evaporator was used. In the rotary evaporator, the flask is installed obliquely to the oil bath and is rotated so that the flask can be uniformly heated to a portion close to the connecting portion. Besides, a portion from the connecting portion of the flask to the condenser is shielded from the outside air by a driving portion, whereby heat exchange with the outside air is substantially minimized. As a result, the internal reflux is minimum, and the retention time can be shortened.

However, the liquid temperature in the rotating flask can not be measured. Namely, in order to shorten the retention time, the amount of charge is intentionally reduced as compared with the size of the flask, whereby even if a thermometer may be inserted, the liquid temperature can not be constantly measured, since the liquid surface is always in the vicinity of the inner wall of the flask. Further, the flask is in rotation, and at the final stage of evaporation, organic acid A and its ammonium salt will solidify, whereby it is difficult to measure the temperature in the flask.

The ammonium salt of acid B undergoes pyrolysis, whereby it is difficult to measure the physical property such as the boiling point accurately. However, the present inventor considered that theoretically, a boiling point is necessarily present, and a phenomenon such as sublimation takes place, whereby it may simply be that one due to pyrolysis can not be distinguished from the contribution of vaporization or sublimation. Therefore, a test was carried out in which the ammonium salt of acid B was evaporated in a reduced pressure system by shortening the retention time. Test Examples 2-6, 2-7 and 2-8 are tests in which a rotary evaporator was used.

In Test Example 2-6, it has been found that by sufficiently reducing the pressure and using an oil bath i.e. a heat source of about 110° C., ammonium acetate can be vaporized. This is a phenomenon at a temperature of not higher than the melting point, and it is assumed that sublimation took place. In Test Example 2-7, ammonium acetate was adequately vaporized even under a relatively mild reduced pressure condition at a level of 150 mmHg. In a practical process, the retention time can be shortened, and it has been proved that a design can be made under this condition. However, in this test, for the purpose of comparison, the retention time was prolonged to correspond to Test Example 2-6 while the oil bath i.e. the heat source was set at 180° C., whereby amidation took place to some extent. This indicates that if the temperature of the heat source is made high, the retention time must be shortened correspondingly.

In Test Example 2-9, water evaporated quickly, whereby it was difficult to determine the factor for the suppression of amidation i.e. whether it was due to a short time or it was due to suppression of dehydration reaction by the presence of water. However, it has been confirmed that both effects contributed substantially and that amidation can be lowered by the presence of water.

Accordingly, as a method for vaporizing acid B after concentrating the crystallization mother liquor, one having a short heating time is preferred. Further, it is preferred to vaporize under a superheated state i.e. to heat the process fluid under a reduced pressure condition by a sufficiently high temperature heat source.

Example 3

Text Example 3-1

Test to Confirm the Presence of Ammonium Acetate (Separation by a Rotary Evaporator)

6.0 g of acetic acid manufactured by Wako Pure Chemical Industries, Ltd., 15.18 g of ammonium succinate manufactured by Wako Pure Chemical Industries, Ltd. and 20 g of water were put into a 200 ml eggplant type flask and installed in a rotary evaporator. The pressure was reduced to 50 mmHg, and the flask was heated by immersing it in an oil bath heated to 140° C. The distillation time was 5 minutes. At a condenser portion, white solid was precipitated and deposited. The bottom was 20.8 g. The composition of this solid was 56.1 wt % (0.099 mol) of succinic acid, 19.6 wt % (0.068 mol) of acetic acid and 15.4 wt % (0.189 mol) of ammonia.

Text Example 3-2

Reactive Crystallization

Using a 100 ml reagent bottle, 4.5 g (0.03 mol) of diammonium succinate was mixed with 30 g (0.5 mol) of acetic acid under heating and dissolved at 80° C. This solution was left to stand at room temperature (17° C.) for 2 hours. White solid precipitated, and this solid was collected by filtration. The recovered solid was 1.92 g, and as a result of the analysis, it was confirmed to comprise 96 wt % of acetic acid and 1 wt % of ammonia.

Text Example 3-3

Gas/Liquid Separation and Concentration after Crystallization 120 g of acetic acid manufactured by Wako Pure Chemical Industries, Ltd. and 30 g of ammonium succinate manufactured by Wako Pure Chemical Industries, Ltd. were mixed, heated and completely dissolved to obtain a solution, which was designated as a crystallization mother liquor. Further,

| | | |
|---|---|---|
| Succinic acid primary pKa: | | 4.21 |
| Succinic acid secondary pKa: | | 5.64 |
| Acetic acid pKa: | | 4.76. |

Accordingly, it is considered that while

| | | |
|---|---|---|
| Charge: | Acetic acid | 120 g 2 mol |
| | Diammonium succinate | 30.4 g 0.2 mol (about 20 wt %), the diammonium succinate is reacted with acetic acid to form approximately the following composition (as ammonia: 2 wt %). |
| Dissolved liquid: | Acetic acid | 108 g 1.8 mol |
| | Monoammonium succinate | 27 g 0.2 mol |
| | Ammonium acetate | 15.4 g 0.2 mol |

This solution was put into a 200 ml eggplant type flask, installed in a simple distillation apparatus and subjected to simple distillation at 150 mmHg. A condenser of water cooling type was used. A very small amount of nitrogen gas was constantly circulated to the simple distillation apparatus for the purpose of preventing bumping and for the purpose of increasing the distillation efficiency.

When the temperature in the flask became 85° C., distillation started, and after the temperature of the oil bath became 105° C., distillation was carried out while reducing the pressure by 10 mmHg each time. For 1 hour and 45 minutes, the distilled amount became 40 ml. Here, the first distillate sample was recovered. The temperature in the flask at that time was 89° C., and the pressure was 120 mmHg.

Thereafter, an operation of reducing the pressure when the distillation stopped, was repeated so that the temperature in the flask would not exceed 100° C. The operation was carried out so that the temperature of the oil bath would not exceed the melting point (114° C.) taking into consideration a fluctuation or error of the thermometer, and 109° C. was the maximum. Over a period of 1 hour and 34 minutes from the first sampling (overall time: 3 hours and 19 minutes), 40 ml was distilled, whereupon a sample was collected. The temperature in the flask at that time was 95° C., and the pressure was 60 mmHg.

The pressure was returned to atmospheric pressure, and the bottom sample was collected. The amount of the content of the flask was 64.96 g from deduction of the tare of the flask and the balance between before and after the test. No precipitation of crystals was observed throughout the period of the simple distillation.

In the composition of the first distillate, acetic acid was 102% (exceeded 100% due to an analytical error); in the composition of the second distillate, acetic acid was 103% (exceeded 100% due to an analytical error), and in the composition of the final bottom, acetic acid was 54%, acetamide 0.4%, succinic acid 34%, succinic acid monoamide 1.8%, and ammonia 9.8%.

Text Example 3-4

Gas/Liquid or Gas/Solid Separation to Obtain a di/Tricarboxylic Acid and its Ammonium Salt Vaporization of ammonium acetate in an acetic acid-succinic acid system was investigated by means of the following model solution.

30.00 g of acetic acid manufactured by Wako Pure Chemical Industries, Ltd., 15.18 g of ammonium succinate manufactured by Wako Pure Chemical Industries, Ltd. and further 7.71 g of ammonium acetate in order to more accurately grasp the vaporization of ammonium acetate manufactured by Wako Pure Chemical Industries, Ltd., were put into a 200 ml eggplant type flask, and installed in a rotary evaporator. The pressure was reduced to 50 mmHg, and the flask was immersed in an oil bath heated to 100° C., whereupon the oil bath was heated to 140° C. When the oil bath reached 132° C., distillation started. The distillation time was 17 minutes.

At a condenser portion, white solid was precipitated and deposited. The bottom was 22.71 g.

The composition of the bottom was 34% of acetic acid, 0.3% of acetamide, 54% of succinic acid, 0.7% of succinic acid monoamide and 12.7% of ammonia.

Text Example 3-5

Conditions for Amidation 120 g of Acetic Acid Manufactured by Wako Pure Chemical Industries, Ltd. and 30 g of ammonium succinate manufactured by Wako Pure Chemical Industries, Ltd. were mixed, heated and completely dissolved to obtain a solution, which was designated as a crystallization mother liquor. Further,

| | | |
|---|---|---|
| Succinic acid primary pKa: | 4.21 | |
| Succinic acid secondary pKa: | 5.64 | |
| Acetic acid pKa: | 4.76. | |

Accordingly, it is considered that while

| | | | |
|---|---|---|---|
| Charge: | Acetic acid | 120 g | 2 mol |
| | Diammonium succinate | 30.4 g | 0.2 mol (about 20 wt %), the diammonium succinate is reacted with acetic acid to form approximately the following composition: |
| Dissolved liquid: | Acetic acid | 108 g | 1.8 mol |
| | Monoammonium succinate | 27 g | 0.2 mol |
| | Ammonium acetate | 15.4 g | 0.2 mol |

This solution was put into a 200 ml eggplant type flask, installed in a simple distillation apparatus and subjected to simple distillation at 380 mmHg. A condenser of water cooling type was used. A very small amount of nitrogen gas was constantly circulated to the simple distillation apparatus for the purpose of preventing bumping and for the purpose of increasing the distillation efficiency.

When the temperature in the flask reached 110° C., the first one drop was distilled, but thereafter, due to internal reflux by heat release, the distillation decreased remarkably. Over a period of 1 hour and 40 minutes from the first one drop, the distilled amount became 40 ml (which corresponds to Test Example 3-1). Here, a first distillate sample was recovered. The temperature at that time was 118° C. When further 40 ml was distilled (132° C.; overall time: 3 hours and 47 minutes), the pressure was once returned to atmospheric pressure, whereupon a second distillate sample and 2.55 g of a bottom sample were collected. Further, the pressure was reduced to 380 mmHg once again, and when 2.97 g was distilled, the distillation was terminated. The amount of the content in the flask was 54.47 g from deduction of the tare of the flask and the balance between before and after the test. No precipitation of crystals was observed throughout the period of the simple distillation.

In the composition of the first distillate, acetic acid was 100%; in the composition of the second distillate, acetic acid was 97% (substantially 100% within an error range), and in the composition of the bottom at the time of sampling the second distillate, was 49% of acetic acid, 7.3% of acetamide, 18% of succinic acid, 16% of succinic acid monoamide and 6.1% of ammonia.

Example 4

In the following, for ammonium acetate, sodium acetate and potassium acetate, high grade reagents manufactured by Wako Pure Chemical Industries, Ltd. were used.

Text Example 4-1

15.22 g (0.198 mol) of ammonium acetate, 20.01 g of deionized water and 5.20 g of 28% aqueous ammonia, manufactured by Wako Pure Chemical Industries, Ltd. (0.086 mol as ammonia) were put into a 200 ml flask and installed in a simple distillation apparatus. The pressure was reduced to 150 mmHg, and the flask was immersed in an oil bath heated to 90° C. When the liquid temperature in the flask became 62° C., distillation started. When the liquid temperature in the flask became 75° C., the distillate was sampled. The distillate was sampled. The amount was 15.79 g. Then, the pressure was reduced to 100 mmHg, to obtain 3.35 g of a distillate and 18.54 g of a bottom.

Acetic acid contained in the first distillate was 0.34 wt %, the acetic acid contained in the second distillate was 0.72 wt %, and acetic acid contained in the bottom was 62.4 wt % (0.193 mol). Ammonia in the bottom was 13.9 wt % (0.152 mol).

From this result, it has been proved that acetic acid is present in the form of ammonium acetate, which is not substantially vaporized at a temperature of not higher than the melting point (114° C.) of ammonium acetate, whereby aqueous ammonia can be separated.

Text Example 4-2

Figure 6:
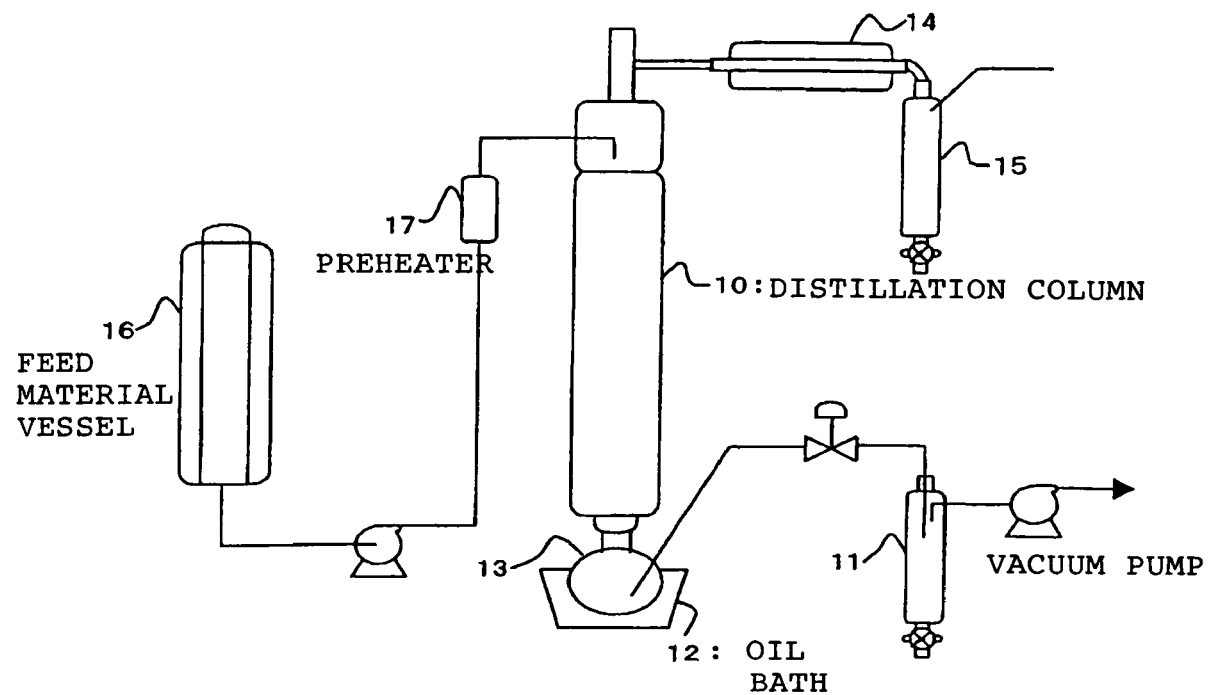
FIG. 6 is a flowchart showing the construction of the apparatus employed in Test Examples 2-2 and 2-3.

A test was carried out by a test apparatus shown in FIG. 6.

As a distillation column 10, an Oldarshow distillation column having 20 plates, was used. In order to improve the liquid hold and the distillation efficiency, an inert gas from a steel bottle 11 was circulated to this distillation column 10 via column bottom flask 13 immersed in an oil bath 12, and a non-condensed gas was discharged into a draft from a gas purge line 15 via a condenser 14.

The charge was 249.9 g of ammonium acetate, 150.0 g of sodium acetate and 250.0 g of deionized water and was preliminarily heated to 90° C. in a feed material tank 16 equipped with a temperature-keeping means. The capacity of the flask 13 at the column bottom was 500 ml, and for startup, 30.06 g of ammonium acetate, 20.27 g of sodium acetate and 70.16 g of acetic acid were charged.

When the inner temperature of the column bottom flask 13 became 120° C., the feed material in the feed material tank 16 was supplied at a flow rate of 165 cc/hr from the top of the distillation column 10 via a preheater 17. At that time, the temperature of the preheater 17 was 110° C.

After an operation for 51 minutes from the initiation of the supply of the feed material, 63.6 g of the distillate and 120.5 g of the bottom in the flask were withdrawn as the first withdrawal. After an operation for further 37 minutes, 43.9 g of the distillate and 71.1 g of the bottom in the flask were withdrawn as the second withdrawal.

Thereafter, a steady state was assumed.

Further, after an operation for 36 minutes, 44.5 g of the distillate and 60.3 g of the bottom in the flask were taken out as the first analytical samples. After an operation for further 36 hours, 46.3 g of the distillate and 74.5 g of the bottom in the flask were taken out as the second analytical samples.

The compositions of the respective analytical samples were as shown in Table 4-1.

TABLE 4-1

| Analytical samples | | Acetic acid | Composition (wt %) | | | |
|---|---|---|---|---|---|---|
| | | | Ammonia | Acetamide | Na | Water |
| First | Distillate (44.5 g) | 0.5 | 7.9 | | | Rest |
| | Bottom (60.3 g) | 71.8 | 3.8 | 9.1 | 9.9 | 5.4 (calculated value) |
| Second | Distillate (46.3 g) | 0.5 | 8.2 | | | Rest |
| | Bottom (74.5 g) | 72.6 | 4.0 | 8.1 | 10.1 | 5.2 (calculated value) |

As is apparent from Table 4-1, there is no substantial difference in the composition between the first and second analytical samples, and thus, the operation can be regarded as substantially steady. On the basis that the operation was substantially in a steady state, if the composition of the supplied feed material and the composition of the second analytical samples are compared, the mass balance will be as shown in the following Table 4-2. Here, the supplied material of 165 cc/hr was converted to a unit of g/hr by using the specific gravity of the feed material being 1.14.

Further, the amount of the acetamidated ammonia was obtained by calculation as follows. Namely, as shown in Table 4-1, acetamide in the bottom was 8.1 wt %, which was calculated as ammonia by molar amount, which is then converted to a weight amount to obtain 1.7 g.

TABLE 4-2

| Components | Supplied amount (g/hr) | Distillate (excluding non-condensed gas) (g/hr) | Bottom (withdrawn from the column bottom) (g/hr) | Acetamidated ammonia |
|---|---|---|---|---|
| Acetic acid | 50.3 | 0.2 | 54.1 | — |
| Water | 43.9 | 42.3 | 3.9 | — |
| Ammonia | 9.7 | 3.8 | 3.0 | 1.7 |
| Na | 7.4 | 0.0 | 7.5 | — |

As is apparent from Table 4-2, the total of the analytical values of ammonia is 8.5 g/hr (=3.8+3.0+1.7), which is substantially different from the supplied amount of 9,7 g/hr, and the difference is remarkable as compared with other substances. This is attributable mainly to the fact that a part of ammonia was lost into a draft together with a non-condensed gas, and it was evaporated during the sampling or during the preparation of the standard solution for the analysis.

When it is considered that ammonium acetate and acetamide remaining in the bottom (withdrawn from the column bottom) were not decomposed and distilled, it is apparent that 51.3% of ammonia supplied as ammonium acetate was distilled off or separated as a non-condensed gas, and at the same time, it was possible to obtain acetic acid having an unbelievably low water content and aqueous ammonia containing no acetic acid, by a distillation column having only 20 plates.

Text Example 4-3

Using the test apparatus as shown in FIG. 6, a test was carried out in the same manner as in Test Example 4-2 except that as the feed material, ammonium acetate, sodium acetate and potassium acetate were used, and the amount of the charge of the feed material and the operation conditions were changed.

The charge was 250 g of ammonium acetate, 150.0 g of potassium acetate and 250.0 g of deionized water, and it was preheated to 90° C. To the column bottom flask, for startup, 30.04 g of ammonium acetate, 20.28 g of potassium acetate and 70.27 g of acetic acid were charged.

When the internal temperature of the column bottom flask became 120° C., the feed material was supplied from the column top at a flow rate of 150 cc/hr. At that time, the temperature of the preheater was 110° C.

After an operation for 59 minutes from the initiation of the supply of the feed material, 65.7 g of the distillate and 133.4 g of the bottom in the flask were taken out as the first withdrawal. After an operation for further 40 minutes, 43.5 g of the distillate and 76.2 g of the bottom in the flask were taken out as the second withdrawal.

Thereafter, a steady state was assumed.

Further, after an operation for 40 minutes, 42.6 g of the distillate and 68.5 g of the bottom in the flask were taken out as the first analytical samples. After an operation for further 40 minutes, 43.5 g of the distillate and 68.1 g of the bottom in the flask were taken out as the second analytical samples.

The compositions of the respective analytical samples were as shown in Table 4-3.

TABLE 4-3

| Analytical samples | | Acetic acid | Composition (wt %) | | | |
|---|---|---|---|---|---|---|
| | | | Ammonia | Acetamide | K | Water |
| First | Distillate (42.6 g) | 0.3 | 7.1 | | | Rest |
| | Bottom (68.5 g) | 69.6 | 2.1 | 5.3 | 17.7 | 5.5 (calculated value) |
| Second | Distillate (43.5 g) | 0.3 | 8.7 | | | Rest |
| | Bottom (68.1 g) | 68.3 | 2.1 | 5.0 | 17.5 | 7.1 (calculated value) |

As is apparent from Table 4-3, there is no substantial difference in the composition between the first and second analytical samples, and the operation can be regarded as substantially steady. On the basis that the operation is substantially in a steady state, if the composition of the supplied feed material and the composition of the second analytical samples are compared, the mass balance will be as shown in the following Table 4-4. Here, the supplied material of 150 cc/hr was converted to a unit of g/hr by using the specific gravity of the feed material being 1.14.

Further, the amount of the acetamidated ammonia was obtained by calculation as follows. Namely, as shown in Table 4-3, acetamide in the bottom was 5.0 wt %, which was calculated as ammonia by molar amount, which was converted to a weight to obtain 1.0 g.

TABLE 4-4

| Components | Supplied amount (g/hr) | Distillate (excluding non-condensed gas) (g/hr) | Bottom (withdrawn from the column bottom) (g/hr) | Acetamidated ammonia |
|---|---|---|---|---|
| Acetic acid | 50.6 | 0.1 | 46.5 | — |
| Water | 44.2 | 39.7 | 4.8 | — |
| Ammonia | 9.7 | 3.8 | 1.4 | 1.0 |
| K | 8.0 | 0.0 | 11.9 | — |

As is apparent from Table 4-4, the total of the analytical values of ammonia is 6.2 g/hr (=3.8+1.4+1.0), which is substantially different from the supplied amount of 9.7 g/hr. Like in the case of Test Example 4-2, this is attributable mainly to the fact that a part of ammonia was lost into a draft together with a non-condensable gas, and it was evaporated during the sampling or during the preparation of the standard solution for the analysis. The reason for the substantial difference in the amount of potassium is not clear.

When it is considered that ammonium acetate and acetamide remaining in the bottom (withdrawn from the column bottom) were not decomposed and distilled, it is apparent that 75.4% of ammonia supplied as ammonium acetate was distilled off or separated as a non-condensable gas, and at the same time, it was possible to obtain acetic acid having an unbelievably low water content and aqueous ammonia containing no acetic acid by a distillation column having only 20 plates.

Text Example 4-4

Using the test apparatus as shown in FIG. 6, a test was carried out in the same manner as in Test Example 4-2 except that as the feed material, ammonium acetate and potassium acetate were used, and the amount of the charge of the feed material and the operation conditions were changed.

The charge was 250.1 g of ammonium acetate, 150.1 g of potassium acetate and 160.0 g of deionized water, and it was preheated to 90° C. To the column bottom flask, for startup, 30.1 g of ammonium acetate, 20.1 g of potassium acetate and 70.0 g of acetic acid were charged.

When the internal temperature of the column bottom flask became 138.4° C., the feed material was supplied from the column top at a flow rate of 174 cc/hr. At that time, the temperature of the preheater was 109.5° C.

After an operation for 22 minutes from the initiation of the supply of the feed material, 19.1 g of the distillate and 95.0 g of the bottom in the flask were taken out as the first withdrawal. After an operation for further 37 minutes, 32.0 g of the distillate and 90.4 g of the bottom in the flask were taken out as the second withdrawal.

Thereafter, a steady state was assumed.

Further, after an operation for 35 minutes, 22.8 g of the distillate and 74.6 g of the bottom in the flask were taken out as the first analytical samples. After an operation for further 34 minutes, 28.4 g of the distillate and 77.7 g of the bottom in the flask were taken out as the second analytical samples.

The compositions of the respective analytical samples were as shown in Table 4-5.

TABLE 4-5

| Analytical samples | | Composition (wt %) | | | | |
|---|---|---|---|---|---|---|
| | | Acetic acid | Ammonia | Acetamide | K | Water |
| First | Distillate (22.8 g) | 1.3 | 5.8 | 0.0 | | 93.0 |
| | Bottom (74.6 g) | 68.5 | 2.6 | 4.2 | 16.6 | 8.1 |
| Second | Distillate (28.4 g) | 1.1 | 7.5 | 0.0 | | 91.4 |
| | Bottom (77.7 g) | 68.8 | 2.2 | 3.2 | 18.6 | 7.1 |

As is apparent from Table 4-5, there is no substantial difference in the composition between the first and second analytical samples, and the operation can be regarded as substantially steady. On the basis that the operation was substantially in a steady state, if the composition of the supplied feed material and the composition of the second analytical samples are compared, the mass balance will be as shown in the following Table 4-6. Here, the supplied material of 174 cc/hr was converted to a unit of g/hr by using the specific gravity of the feed material being 1.18.

Further, the amount of the acetamidated ammonia was obtained by calculation as follows. Namely, as shown in Table 4-5, acetamide in the bottom was 2.2 wt %, which was calculated as ammonia by molar amount, which was converted to a weight to obtain 0.72 g.

TABLE 4-6

| Components | Supplied amount (g/hr) | Distillate (excluding non-condensed gas) (g/hr) | Bottom (withdrawn from the column bottom) (g/hr) | Acetamidated ammonia |
|---|---|---|---|---|
| Acetic acid | 59.4 | 0.32 | 53.5 | |
| Water | 33.1 | 25.9 | 5.5 | |
| Ammonia | 11.4 | 2.1 | 1.7 | 0.72 |
| K | 9.2 | 0.0 | 14.4 | |

As is apparent from Table 4-6, the total of the analytical values of ammonia is 4.5 g/hr (=2.1+1.7+0.7), which is substantially different from the supplied amount of 11.4 g/hr. Like in Test Example 4-2, this is attributable mainly to the fact that a part of ammonia was lost into a draft together with a non-condensable gas, and it was evaporated during the sampling or during the preparation of the standard solution for the analysis. The reason for the large difference in the amount of potassium is unclear.

When it is considered that ammonium acetate and acetamide remaining in the bottom (withdrawn from the column bottom) were not decomposed and distilled, it is apparent that 78.7% of ammonia supplied as ammonium acetate, was distilled off or separated as a non-condensable gas, and at the same time, it was possible to obtain acetic acid having an unbelievably low water content and aqueous ammonia containing no acetic acid by a distillation column having only 20 plates.

Text Example 4-5

Using the test apparatus as shown in FIG. 6, a test was carried out in the same manner as in Test Example 4-2 except that as the feed material, ammonium acetate and potassium acetate were used, and the amount of the charge of the feed material and the operation conditions were changed.

The charge was 250.1 g of ammonium acetate, 150.1 g of potassium acetate and 150.0 g of deionized water, and it was preheated to 90° C. In the column bottom flask, for startup, 30.1 g of ammonium acetate, 20.0 g of potassium acetate and 70.1 g of acetic acid were charged.

Upon expiration of 21 minutes from the initiation of the temperature raising, the feed material was supplied from the column top at a flow rate of 160.0 cc/hr. 11 Minutes later, the first distillate was obtained, and the internal temperature of the column bottom flask at that time was 137.2° C., and the temperature of the preheater was 108.5° C.

After an operation for 19 minutes from the initiation of the supply of the feed material, 10.7 g of the distillate and 102.8 g of the bottom in the flask were taken out as the first withdrawal. After an operation for further 30 minutes, 31.1 g of the distillate and 79.8 g of the bottom in the flask were taken out as the second withdrawal.

Thereafter, a steady state was assumed.

Further, after an operation for 37 minutes, 31.8 g of the distillate and 76.9 g of the bottom in the flask were taken out as the first analytical samples. After an operation for further 38 minutes, 31.1 g of the distillate and 79.4 g of the bottom in the flask were taken out as the second analytical samples.

The compositions of the respective analytical samples were as shown in Table 4-7.

TABLE 4-7

| Analytical samples | | Composition (wt %) | | | | |
|---|---|---|---|---|---|---|
| | | Acetic acid | Ammonia | Acetamide | K | Water |
| First | Distillate (31.8 g) | 1.2 | 9.3 | 0.0 | | 89.5 |
| | Bottom (76.9 g) | 70.0 | 3.2 | 4.8 | 16.0 | 6.0 |
| Second | Distillate (31.1 g) | 1.1 | 8.3 | 0.0 | | 90.6 |
| | Bottom (79.4 g) | 69.2 | 2.7 | 4.6 | 17.5 | 6.0 |

As is apparent from Table 4-7, there is no substantial difference in the composition between the first and second analytical samples, and the operation can be regarded as substantially steady. On the basis that the operation was substantially in a steady state, if the composition of the supplied feed material and the composition of the second analytical samples are compared, the mass balance will be as shown in the following Table 4-8. Here, the supplied feed material of 160.0 cc/hr was converted to a unit of g/hr by using the specific gravity of the feed material being 1.20.

Further, the amount of the acetamidated ammonia was obtained by calculation as follows. Namely, as shown in Table 4-7, acetamide in the bottom was 2.2 wt %, which was calculated as ammonia by molar amount, which was converted to a weight to obtain 1.05 g.

TABLE 4-8

| Components | Supplied amount (g/hr) | Distillate (excluding non-condensed gas) (g/hr) | Bottom (withdrawn from the column bottom) (g/hr) | Acetamidated ammonia |
|---|---|---|---|---|
| Acetic acid | 61.0 | 0.35 | 55.0 | |
| Water | 31.9 | 28.2 | 4.7 | |
| Ammonia | 11.7 | 2.6 | 2.1 | 1.05 |
| K | 9.3 | 0.0 | 13.9 | |

As is apparent from Table 4-8, the total of the analytical values of ammonia is 5.6 g/hr (=2.6+2.1+1.1), which is substantially different from the supplied amount of 11.7 g/hr. Like in the case of Test Example 4-2, this is attributable mainly to the fact that a part of ammonia was lost into a draft together with a non-condensable gas, and it was evaporated during the sampling or during the preparation of the standard solution for the analysis. The reason for the large difference in the amount of potassium is unclear.

When it is considered that ammonium acetate and acetamide remaining in the bottom (withdrawn from the column bottom) were not decomposed and distilled, it is apparent that 72.8% of ammonia supplied as ammonium acetate was distilled off or separated as a non-condensable gas, and at the same time, it was possible to obtain acetic acid having an unbelievably low water content and aqueous ammonia containing no acetic acid by a distillation column having only 20 plates.

Comparative Text Example 4-1

15.23 g (0.198 mol) of ammonium acetate, 15.21 g (0.185 mol) of sodium acetate, 5.02 g (0.051 mol) of potassium acetate and 50.01 g of deionized water, were put into a 200 ml flask and installed in a simple distillation apparatus. This was immersed in an oil bath heated to 180° C. When the liquid temperature in the flask became 108° C., distillation started. When the liquid temperature in the flask became 150° C., heating was stopped, and the distillate and the bottom were sampled. The distillation time was 63 minutes. The amount of the distillate was 53.18 g, and the amount of the bottom was 30.28 g. Precipitation started in about 30 minute from the first distillation, whereby it was impossible to measure the pH.

Acetic acid contained in the distillate was 5.47 wt % (0.049 mol), and ammonia was 2.98 wt % (0.093 mol). Acetic acid contained in the bottom was 79.32 wt % (0.400 mol), and ammonia was 0.64 wt %.

If acetic acid present in the form of an alkali metal salt (0.236 mol; from the charged amount) is excluded, it will be 0.164 mol, which indicates that acetic acid in an amount of 24.7% of the ammonium acetate (0.198 mol; from the charged amount) which should be decomposed, was distilled off. A part of ammonia was discharged without being condensed, which is the reason for the unbalance.

Comparative Text Example 4-2

15.22 g (0.198 mol) of ammonium acetate, 10.00 g (0.102 mol) of potassium acetate and 50.05 g of deionized water were put into a 200 ml flask and installed in a simple distillation apparatus. This was immersed in an oil bath heated to 180° C. When the liquid temperature in the flask became 106° C., distillation started. When the liquid temperature in the flask became 150° C., heating was stopped, and the distillate and the bottom were sampled. The distillation time was 51 minutes. The amount of the distillate was 53.19 g, and the amount of the bottom was 20.26 g. Precipitation started immediately after the sampling, whereby it was impossible to measure the pH.

Acetic acid contained in the distillate was 5.05 wt % (0.045 mol), and ammonia was 3.22 wt % (0.101 mol). Acetic acid contained in the bottom was 76.51 wt % (0.258 mol), and ammonia was not detected.

If acetic acid present in the form of an alkali metal salt (0.102 mol; from the charged amount) is excluded, it will be 0.156 mol, which indicates that acetic acid in an amount of 22.7% of the ammonium acetate (0.198 mol; from the charged amount) which should be decomposed, was distilled. A part of ammonia was discharged without being condensed, which is the reason for the unbalance.

Comparative Text Example 4-3

15.20 g (0.197 mol) of ammonium acetate, 5.00 g (0.061 mol) of sodium acetate, 15.00 g (0.153 mol) of potassium acetate and 50.04 g of deionized water, were put into a 200 ml flask and installed in a simple distillation apparatus. This was immersed in an oil bath heated to 180° C. When the liquid temperature in the flask became 108° C., distillation started. When the liquid temperature in the flask became 150° C., heating was stopped, and the distillate and the bottom were sampled. The distillation time was 41 minutes. The amount of the distillate was 52.32 g, and the amount of the bottom was 31.32 g. Precipitation started immediately after the sampling, whereby it was impossible to measure the pH.

Acetic acid contained in the distillate was 5.72 wt % (0.050 mol), and ammonia was 3.68 wt % (0.113 mol). Acetic acid contained in the bottom was 72.21 wt % (0.377 mol), and ammonia was not detected.

If acetic acid present in the form of an alkali metal salt (0.214 mol; from the charged amount) is excluded, it will be 0.163 mol, which indicates that acetic acid in an amount of 25.4% of the ammonium acetate (0.197 mol; from the charged amount) which should be decomposed, was distilled. A part of ammonia was discharged without being condensed, which is the reason for the unbalance.

Comparative Text Example 4-4

15.20 g (0.197 mol) of ammonium acetate, 10.02 g (0.102 mol) of potassium acetate and 15.27 g of deionized water were put into a 200 ml flask and installed in a simple distillation apparatus. This was immersed in an oil bath heated to 180° C. When the liquid temperature in the flask became 116° C., distillation started. When the liquid temperature in the flask became 150° C., heating was stopped, and the distillate and the bottom were sampled. The distillation time was 23 minutes. The amount of the distillate was 16.65 g, and the amount of the bottom was 21.76 g. Precipitation started immediately after the sampling, whereby it was impossible to measure the pH.

Acetic acid contained in the distillate was 8.43 wt % (0.023 mol), and ammonia was 7.00 wt % (0.069 mol). Acetic acid contained in the bottom was 75.62 wt % (0.274 mol), and ammonia was 2.13 wt % (0.027 mol).

If acetic acid present in the form of an alkali metal salt (0.102 mol; from the charged amount) is excluded, it will be 0.172 mol, which indicates that acetic acid in an amount of 11.7% of the ammonium acetate (0.197 mol; from the charged amount) which should be decomposed, was distilled. A part of ammonia was discharged without being condensed, which is the reason for the unbalance.

Comparative Text Example 4-5

15.20 g (0.197 mol) of ammonium acetate, 10.01 g (0.122 mol) of potassium acetate and 15.19 g of deionized water were put into a 200 ml flask and installed in a simple distillation apparatus. This was immersed in an oil bath heated to 180° C. When the liquid temperature in the flask became 116° C., distillation started. When the liquid temperature in the flask became 135° C., precipitation of solid was observed. When the liquid temperature in the flask became 150° C., heating was stopped, and the distillate and the bottom were sampled. The distillation time was 23 minutes. The amount of the distillate was 17.17 g, and the amount of the bottom was 21.25 g. Precipitation started, whereby it was impossible to measure the pH.

Acetic acid contained in the distillate was 11.33 wt % (0.0.32 mol), and ammonia was 6.02 wt % (0.061 mol). Acetic acid contained in the bottom was 83.97 wt % (0.297 mol), and ammonia was 2.13 wt % (0.027 mol).

If acetic acid present in the form of an alkali metal salt (0.122 mol; from the charged amount) is excluded, it will be 0.175 mol, which indicates that acetic acid in an amount of 16.2% of the ammonium acetate (0.197 mol; from the charged amount) which should be decomposed, was distilled. A part of ammonia was discharged without being condensed, which is the reason for the unbalance.

INDUSTRIAL APPLICABILITY

According to the present invention, as is unexpected from the conventional acid/base reaction, it is possible to obtain free organic acid A in solid form, from an ammonium salt of organic acid A having a high melting point, such as a dicarboxylic acid, a tricarboxylic acid or an amino acid, produced by bioconversion of a biogenic carbon source, by reactive precipitation utilizing an acid/base reaction employing weak acid B such as a monocarboxylic acid which is a weaker acid than the organic acid A.

Further, it is possible to recover organic acid A and its ammonium salt by vaporizing and efficiently separating acid B such as a monocarboxylic acid and an ammonium salt of acid B such as an ammonium salt of a monocarboxylic acid, from the crystallization mother liquor after precipitating and separating organic acid A by reactive crystallization. It is possible to increase the efficiency for separation and recovery of the respective substances by preventing side reactions in this vaporization operation. It is possible to recycle and reuse the separated acid B, organic acid A and its ammonium salt, without requiring a cumbersome operation.

Further, a method is presented wherein the separated ammonium salt of acid B such as an ammonium salt of a monocarboxylic acid, is decomposed into acid B such as a monocarboxylic acid and ammonia by means of an alkali metal or alkaline earth metal salt. At that time, it is possible to readily separate water present in the reaction system and acid B such as a monocarboxylic acid and to efficiently recover acid B having a low water content and aqueous ammonia containing no such acid.

The entire disclosures of Japanese Patent Application No. 2002-135656 filed on May 10, 2002, Japanese Patent Application No. 2002-231740 filed on Aug. 8, 2002, Japanese Patent Application No. 2002-231741 filed on Aug. 8, 2002 and Japanese Patent Application No. 2002-305989 filed on Oct. 21, 2002 including specifications, claims, drawings and summaries are incorporated herein by reference in their entireties.

What is claimed is:

1. A method for producing an organic acid A, which method comprises subjecting an ammonium salt of said organic acid A to reactive crystallization with an acid B, wherein said organic acid A has a pKa(A) and said acid B has a pKa(B) which satisfy the following formula (1):

$$pKa(A) \leq pKa(B) \quad (1)$$

where pKa(A) and pKa(B) represent ionization indices of said organic acid A and said acid B, respectively, provided that when either of said organic acid A or said acid B have plural ionization index values, pKa(A) and pKa(B) represent the minimum pKa among them,
to precipitate said organic acid A in solid form,
wherein said ammonium salt of said organic acid A is obtained by a process comprising bioconversion of a carbon source by a microorganism in the presence of at least one neutralizing agent selected from the group consisting of ammonia, ammonium carbonate, and urea, to obtain said ammonium salt of said organic acid.

2. The method according to claim 1, wherein said acid B is volatile.

3. The method according to claim 1, wherein said organic acid A is an organic acid having a melting point of at least 120° C.

4. The method according to claim 1, wherein said organic acid A is a $C_{4-12}$ dicarboxylic or tricarboxylic acid, or a $C_{4-12}$ amino acid.

5. The method according to claim 1, wherein said acid B is a monocarboxylic acid.

6. The method according to claim 1, wherein said acid B is acetic acid or propionic acid.

7. The method according to claim 1, wherein said reactive crystallization is carried out in a single stage or in multi-stages, and the pH is from 2.1 to 6.5 in at least one stage.

8. The method according to claim 1, wherein said bioconversion affords a reaction solution, and wherein said process further comprises concentrating said reaction solution, to obtain a concentrate, and wherein said concentrate is subjected to said reactive crystallization.

9. The method according to claim 1, further comprising:
separating said organic acid A precipitated by said reactive crystallization, to obtain a crystallization mother liquor; and, after said separating, decomposing an ammonium salt of said acid B in said crystallization mother liquor to obtain acid B; and recycling said obtained acid B for use as a solvent for said reactive crystallization.

10. The method according to claim 9, wherein said organic acid A precipitated by said reactive crystallization is separated, to obtain a crystallization mother liquor; after the separation, said crystallization mother liquor is concentrated by vaporizing acid B therefrom; and then, said acid B and its ammonium salt are decomposed/vaporized in order to recover organic acid A and its ammonium salt.

11. The method according to claim 10, wherein said vaporizing of acid B is carried out at a temperature of not higher than the melting point of the ammonium salt of acid B.

12. The method according to claim 10, wherein said acid B and its ammonium salt are decomposed/vaporized by heating under a reduced pressure of from 0.001 mmHg to 200 mmHg.

13. The method according to claim 9, wherein said decomposing comprises heating a liquid comprising said ammonium salt of said acid B, an alkali metal and/or alkaline earth metal salt of said acid B, and water, and withdrawing a gas of a basic aqueous solution, and subjecting said basic aqueous solution withdrawn, directly or after condensation, to gas/liquid separation, gas/solid separation or gas/liquid/solid separation at a temperature of not higher than the melting point of said ammonium salt of said acid B.

14. The method according to claim 9, wherein said decomposing comprises heating a liquid comprising said ammonium salt of said acid B, an alkali metal and/or alkaline earth metal salt of said acid B, and water, by supplying said liquid to a distillation column having at least two plates as the real number of plates, and withdrawing a gas of a basic aqueous solution from the top of said distillation column.

15. The method according to claim 14, wherein in said heating, said liquid comprising said ammonium salt of said acid B, an alkali metal and/or alkaline earth metal salt of said acid B, and water, is supplied to a site of said distillation column having at least two plates as the real number of plates, where the temperature is not higher than the melting point of said ammonium salt of said acid B.

16. The method according to claim 13, wherein said alkali metal and/or alkaline earth metal salt of said acid B, contains an alkali metal and/or an alkaline earth metal which is at least one member selected from the group consisting of Na, K, Ca and Mg.

17. The method according to claim 13, wherein the liquid after said withdrawing the gas of a basic aqueous solution, is subjected to a separation step which is carried out under reduced pressure or atmospheric pressure at a temperature of at least 125° C., to separate and recover said acid B.

18. The method according to claim 17, wherein residual liquid after the separation step is mixed with a system comprising water to hydrolyze an amide compound formed as a byproduct in the heating step and the separation step and then recycled to the heating step.

19. The method according to claim 1, wherein said neutralizing agent comprises ammonia;
and said method further comprises:
separating said organic acid A precipitated by said reactive crystallization, to obtain a crystallization mother liquor; and after said separating, decomposing an ammonium salt of said acid B in said crystallization mother liquor, to obtain ammonia; and recycling the obtained ammonia as a neutralizing agent for said bioconversion.

20. The method according to claim 1, wherein said reactive crystallization is carried out in multi-stages, and in reactive crystallization in a second or subsequent stage, a crystallization mother liquor obtained after separating said precipitated organic acid A is, directly or after concentrating an ammonium salt of said acid B by vaporization of the reactive crystallization solvent containing said acid B, or after separating said organic acid A or its salt dissolved in said crystallization mother liquor, recycled to a crystallizer for reactive crystallization in a preceding stage.

21. A method for producing an organic acid A, which method comprises subjecting an ammonium salt of said organic acid A to reactive crystallization with an acid B, wherein said organic acid A has a pKa(A) and said acid B has a pKa(B) which satisfy the following formula (1):

$$pKa(A) \leq pKa(B) \quad (1)$$

where pKa(A) and pKa(B) represent ionization indices of said organic acid A and said acid B, respectively, provided that when either of said organic acid A or said acid B have plural ionization index values, pKa(A) and pKa(B) represent the minimum pKa among them, to precipitate said organic acid A in solid form, wherein said ammonium salt of said organic acid A is obtained in the form of an aqueous solution of said ammonium salt of said organic acid A, by a process comprising:

obtaining a reaction solution containing an alkali metal and/or alkaline earth metal salt of said organic acid A by bioconversion of a carbon source by a microorganism in the presence of at least one neutralizing agent selected from the group consisting of an alkali metal hydroxide, an alkaline earth metal hydroxide, an alkali metal carbonate, and an alkaline earth metal carbonate;

adding ammonia and carbon dioxide, and/or ammonium carbonate to said reaction solution containing an alkali metal and/or alkaline earth metal salt of said organic acid A to carry out reactive crystallization and to precipitate an alkali metal and/or alkaline earth metal carbonate; and separating the precipitated carbonate.

22. The method according to claim 21, wherein said acid B is volatile.

23. The method according to claim 21, wherein said organic acid A is an organic acid having a melting point of at least 120° C.

24. The method according to claim 21, wherein said organic acid A is a $C_{4-12}$ dicarboxylic or tricarboxylic acid, or a $C_{4-12}$ amino acid.

25. The method according to claim 21, wherein said acid B is a monocarboxylic acid.

26. The method according to claim 21, wherein said acid B is acetic acid or propionic acid.

27. The method according to claim 21, wherein said reactive crystallization is carried out in a single stage or multi-stages, and the pH is from 2.1 to 6.5 at least in one stage.

28. The method according to claim 21, wherein said bioconversion affords a reaction solution, and wherein said process further comprises concentrating said reaction solution, to obtain a concentrate, and wherein said concentrate is subjected to said reactive crystallization.

29. The method according to claim 21, further comprising:

separating said organic acid A precipitated by said reactive crystallization, to obtain a crystallization mother liquor; and, after said separating, decomposing an ammonium salt of said acid B in said crystallization mother liquor to obtain acid B; and recycling said obtained acid B for use as a solvent for said reactive crystallization.

30. The method according to claim 29, wherein said organic acid A precipitated by said reactive crystallization is separated, to obtain a crystallization mother liquor; after the separation, said crystallization mother liquor is concentrated by vaporizing acid B therefrom; and then, said acid B and its ammonium salt are decomposed/vaporized in order to recover organic acid A and its ammonium salt.

31. The method according to claim 30, wherein said vaporizing of acid B is carried out at a temperature of not higher than the melting point of the ammonium salt of acid B.

32. The method according to claim 30, wherein said acid B and its ammonium salt are decomposed/vaporized by heating under a reduced pressure of from 0.001 mmHg to 200 mmHg.

33. The method according to claim 29, wherein said decomposing comprises heating a liquid comprising said ammonium salt of acid B, an alkali metal and/or alkaline earth metal salt of said acid B, and water, and withdrawing a gas of a basic aqueous solution, and subjecting said basic aqueous solution withdrawn, directly or after condensation, to gas/liquid separation, gas/solid separation or gas/liquid/solid separation at a temperature of not higher than the melting point of said ammonium salt of acid B.

34. The method according to claim 29, wherein said decomposing comprises heating a liquid comprising said ammonium salt of said acid B, an alkali metal and/or alkaline earth metal salt of said acid B, and water, by supplying said liquid to a distillation column having at least two plates as the real number of plates, and withdrawing a gas of a basic aqueous solution from the top of said distillation column.

35. The method according to claim 34, wherein in said heating, said liquid comprising said ammonium salt of said acid B, an alkali metal and/or alkaline earth metal salt of said acid B, and water, is supplied to a site of said distillation column having at least two plates as the real number of plates, where the temperature is not higher than the melting point of said ammonium salt of said acid B.

36. The method according to claim 33, wherein said alkali metal and/or alkaline earth metal salt of said acid B, contains an alkali metal and/or an alkaline earth metal which is at least one member selected from the group consisting of Na, K, Ca and Mg.

37. The method according to claim 33, wherein the liquid after said withdrawing the gas of a basic aqueous solution, is subjected to a separation step which is carried out under reduced pressure or atmospheric pressure at a temperature of at least 125° C., to separate and recover said acid B.

38. The method according to claim 21, wherein residual liquid after the separation step is mixed with a system comprising water to hydrolyze an amide compound formed as a byproduct in the heating step and the separation step and then recycled to the heating step.

39. The method according to claim 21, further comprising:

separating said organic acid A precipitated by said reactive crystallization, to obtain a crystallization mother liquor; and, after said separating, decomposing an ammonium salt of said acid B in said crystallization mother liquor, to obtain ammonia; and using the obtained ammonia as an ammonia source for said reactive crystallization of said alkali metal and/or alkaline earth metal carbonate.

40. The method according to claim 21, wherein said reactive crystallization is carried out in multi-stages, and in reactive crystallization in a second or subsequent stage, a crystallization mother liquor obtained after separating said precipitated organic acid A is, directly or after concentrating an ammonium salt of said acid B by vaporization of the reactive crystallization solvent containing said acid B, or after separating said organic acid A or its salt dissolved in said crystallization mother liquor, recycled to a crystallizer for reactive crystallization in a preceding stage.

* * * * *

UNITED STATES PATENT AND TRADEMARK OFFICE
CERTIFICATE OF CORRECTION

PATENT NO. : 7,217,837 B2
APPLICATION NO. : 10/976822
DATED : May 15, 2007
INVENTOR(S) : Atsushi Isotani It is certified that error appears in the above-identified patent and that said Letters Patent is hereby corrected as shown below:

Column 52, TABLE 4-3, "

TABLE 4-3

| Analytical samples | | Acetic acid | Ammonia | Acetamide | K | Water |
|---|---|---|---|---|---|---|
| First | Distillate (42.6 g) | 0.3 | 7.1 | | | Rest |
| | Bottom (68.5 g) | 69.6 | 2.1 | 5.3 | 17.7 | 5.5 (calculated value) |
| Second | Distillate (43.5 g) | 0.3 | 8.7 | | | Rest |
| | Bottom (68.1 g) | 68.3 | 2.1 | 5.0 | 17.5 | 7.1 (calculated value) |

"

should read --

TABLE 4-3

| Analytical samples | | Acetic acid | Ammonia | Acetamide | K | Water |
|---|---|---|---|---|---|---|
| First | Distillate (42.6 g) | 0.3 | 7.1 | | | Rest |
| | Bottom (68.5 g) | 69.6 | 2.1 | 5.3 | 17.7 | 5.5 (calculated value) |
| Second | Distillate (43.5 g) | 0.3 | 8.7 | | | Rest |
| | Bottom (68.1 g) | 68.3 | 2.1 | 5.0 | 17.5 | 7.0 (calculated value) |

--.

Signed and Sealed this

Twenty-sixth Day of August, 2008

JON W. DUDAS
*Director of the United States Patent and Trademark Office*